United States Patent [19]

Abbott et al.

[11] Patent Number: 4,537,717

[45] Date of Patent: Aug. 27, 1985

[54] DERIVATIVES OF A-21978C CYCLIC PEPTIDES

[75] Inventors: Bernard J. Abbott, Greenwood; Manuel Debono, Indianapolis; David S. Fukuda, Brownsburg, all of Ind.

[73] Assignee: Eli Lilly and Company, Ind.

[21] Appl. No.: 652,695

[22] Filed: Sep. 21, 1984

Related U.S. Application Data

[63] Continuation of Ser. No. 573,901, Jan. 26, 1984, abandoned, which is a continuation of Ser. No. 493,447, May 11, 1983, abandoned, which is a continuation-in-part of Ser. No. 382,012, May 21, 1982, abandoned.

[51] Int. Cl.$^3$ .................................................. C07C 103/52
[52] U.S. Cl. .................................................. 260/112.5 R
[58] Field of Search ................................. 260/112.5 R

[56] References Cited

U.S. PATENT DOCUMENTS

| | | | |
|---|---|---|---|
| 3,150,059 | 9/1964 | Kleinschmidt et al. | 260/112.5 R |
| 4,050,989 | 9/1977 | Kuwana et al. | 260/112.5 R |
| 4,208,403 | 6/1980 | Hamill et al. | 424/115 |
| 4,287,120 | 9/1981 | Abbott et al. | 260/112.5 R |
| 4,293,482 | 10/1981 | Abbott et al. | 260/112.5 R |
| 4,320,052 | 3/1982 | Abbott et al. | 260/112.5 R |
| 4,320,053 | 3/1982 | Abbott et al. | 260/112.5 R |
| 4,320,054 | 3/1982 | Abbott et al. | 260/112.5 R |
| 4,322,338 | 3/1982 | Abbott et al. | 260/112.5 R |

FOREIGN PATENT DOCUMENTS 405867 7/1963 Japan ............................. 260/112.5 R

OTHER PUBLICATIONS

T. Kato et al., *J. Antibiotics* 29 (12) 1339-1340 (1976).
S. Chihara et al., *Agr. Biol. Chem.* 37 (11) 2455-2463 (1973).
S. Chihara et al., ibid. 37 (12) 2709-2717 (1973).
S. Chihara et al., ibid. 38 (3), 521-529 (1974).
S. Chihara et al., ibid. 38 (10) 1767-1777 (1974).
T. Suzuki et al., *J. Biochem.* 56 (4) 335-343 (1964).
J. M. Weber et al., *J. Antibiotics* 31 (4) 373-374 (1978).
J. Shoji et al., ibid. 28, 764-769 (1975).
J. Shoji et al., ibid. 29 (4) 380-389 (1976).
J. Shoji et al., ibid. 29 (12) 1268-1274 (1976).
J. Shoji et al., ibid. 29 (12) 1275-1280 (1976).

*Primary Examiner*—Delbert R. Phillips
*Attorney, Agent, or Firm*—Nancy H. Harrison, Arthur R. Whale

[57] ABSTRACT

A-21978C cyclic peptide derivatives of the formula

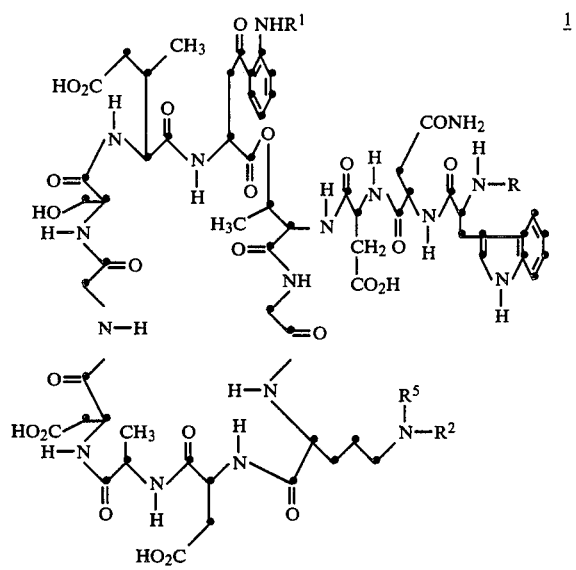

in which R, $R^1$ and $R^2$ are, independently, hydrogen, $C_4$–$C_{14}$-alkyl, optionally substituted $C_2$–$C_{19}$-alkanoyl, $C_5$–$C_{19}$-alkenoyl or an amino-protecting group; $R^3$, $R^4$ and $R^5$ are hydrogen or (i) $R^3$ and $R^1$ and/or (ii) $R^4$ and R and/or (iii) $R^5$ and $R^2$, taken together, may represent a $C_4$–$C_{14}$ alkylidene group; provided that (1) at least one of R, $R^1$ or $R^2$ must be other than hydrogen or an amino-protecting group, (2) at least one of $R^1$ or $R^2$ must be hydrogen or an amino-protecting group, (3) the R, $R^1$ and $R^2$ groups must together contain at least four carbon atoms, and (4) when $R^1$ and $R^2$ are both selected from hydrogen or an amino-protecting group, R cannot be 8-methyldecanoyl, 10-methyldodecanoyl, 10-methylundecanoyl, the mixed $C_{10}$-alkanoyl group of A-21978$C_0$ or the specific $C_{12}$-alkanoyl groups of A-21978C factors $C_4$ and $C_5$; and the salts thereof.

30 Claims, No Drawings

DERIVATIVES OF A-21978C CYCLIC PEPTIDES

CROSS-REFERENCE TO RELATED APPLICATION

This applicaton is a continuation of application Ser. No. 573,901, filed 1/26/84, abandoned, which is a continuation of application Ser. No. 493,447, filed 5/11/83, now abandoned, which is a continuation-in-part of application Ser. No. 382,012, filed 5/21/82 now abandoned.

SUMMARY OF THE INVENTION

This invention relates to derivatives of A-21978C cyclic peptides which have formula 1:

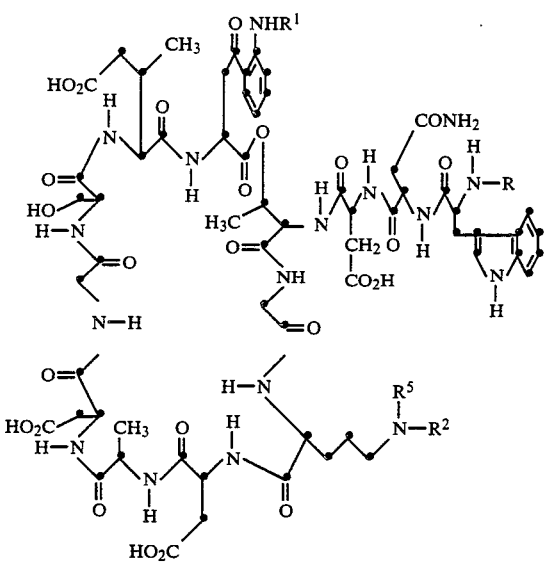

in which R, $R^1$ and $R^2$ are, independently, hydrogen, $C_4$–$C_{14}$-alkyl, optionally substituted $C_2$–$C_{19}$-alkanoyl, $C_5$–$C_{19}$-alkenoyl or an amino-protecting group; $R^3$, $R^4$ and $R^5$ are hydrogen or (i) $R^3$ and $R^1$ and/or (ii) $R^4$ and R and/or (iii) $R^5$ and $R^2$, taken together, may represent a $C_4$–$C_{14}$alkylidene group; provided that (1) at least one of R, $R^1$ or $R^2$ must be other than hydrogen or an amino-protecting group, (2) at least one of $R^1$ or $R^2$ must be hydrogen or an amino-protecting group, (3) the R, $R^1$ and $R^2$ groups must together contain at least four carbon atoms, and (4) when $R^1$ and $R^2$ are both selected from hydrogen or an amino-protecting group, R cannot be 8-methyldecanoyl, 10-methylundecanoyl, 10-methyldodecanoyl, the mixed $C_{10}$-alkanoyl group of A-21978C factor $C_0$ or the specific $C_{12}$-alkanoyl groups of A-21978C factors $C_4$ and $C_5$; and the salts of these peptides. The A-21978C cyclic peptide derivatives and salts of this invention are useful semi-synthetic antibacterial agents or intermediates to such agents.

DETAILED DESCRIPTION OF THE INVENTION

In this specification the following abbreviations, most of which are commonly known in the art, are used:
Ala: alanine
Asp: aspartic acid
Gly: glycine
Kyn: kynurenine
Orn: ornithine
Ser: serine
Thr: threonine
Trp: tryptophan
t-BOC: tert-butoxycarbonyl
Cbz: benzyloxycarbonyl
DMF: dimethylformamide
THF: tetrahydrofuran
HPLC: high performance liquid chromatography
NMR: $^1$H nuclear magnetic resonance
TLC: thin-layer chromatography
UV: ultraviolet

FIELD OF THE INVENTION

Although there are many known antibacterial agents, the need for improved antibiotics continues. Antibiotics differ in their effectiveness against pathogenic organisms. Organism strains which are resistant to known antibiotics continually develop. In addition, individual patients often suffer serious reactions to specific antibiotics, due to hypersensitivity and/or to toxic effects. There is, therefore, a continuing need for new and improved antibiotics.

THE PRIOR ART

The A-21978C antibiotics are closely related, acidic peptide antibiotics. Members of this class of antibiotics which were previously known include crystallomycin, amphomycin, zaomycin, aspartocin, and glumamycin [see T. Korzbyski, Z. Kowszyk-Gindifer and W. Kurylowicz, "Antibiotics-Origin, Nature and Properties," Vol. I, Pergamon Press, New York, N.Y., 1967, pp. 397–401 and 404–408]; tsushimycin [J. Shoji, et al., J. Antibiotics 21, 439–443 (1968)]; laspartomycin [H. Naganawa, et al., J. Antibiotics, 21, 55–62 (1968)]; brevistin [J. Shoji and T. Kato, J. Antibiotics 29, 380–389 (1976)]; cerexin A [J. Shoji, et al., J. Antibiotics 29, 1268–1274 (1976)] and cerexin B [J. Shoji and T. Kato, J. Antibiotics 29, 1275–1280 (1976)]. Of these antibiotics, brevistin, cerexin A and cerexin B appear to be most closely related to the A-21978C antibiotics.

The A-21978C antibiotics are described by Robert L. Hamill and Marvin M. Hoehn in U.S. Pat. No. 4,208,403, issued June 7, 1980, which is incorporated herein by reference. As described in U.S. Pat. No. 4,208,403, the A-21978 antibiotic complex contains a major component, factor C, which is itself a complex of closely related factors. A-21978 factor C, which is called the A-21978C complex, contains individual factors $C_0$, $C_1$, $C_2$, $C_3$, $C_4$ and $C_5$. Factors $C_1$, $C_2$ and $C_3$ are major factors; and factors $C_0$, $C_4$ and $C_5$ are minor factors. The structure of the A-21978C factors is shown in formula 2:

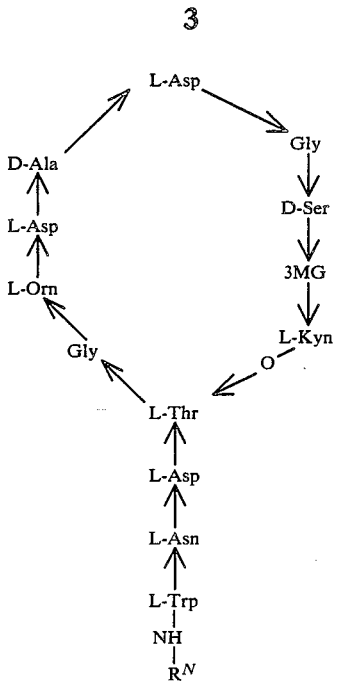

wherein 3MG represents L-threo-3-methylglutamic acid, and $R^N$ represents a specific fatty acid moiety. The specific $R^N$ groups of the factors are as follows:

| A-21978C Factor | $R^N$ Moiety |
|---|---|
| $C_1$ | 8-methyldecanoyl |
| $C_2$ | 10-methylundecanoyl |
| $C_3$ | 10-methyldodecanoyl |
| $C_0$ | $C_{10}$-alkanoyl* |
| $C_4$ | $C_{12}$-alkanoyl* |
| $C_5$ | $C_{12}$-alkanoyl* |

*Identity not yet determined

Kleinschmidt et al. in U.S. Pat. No. 3,150,059, issued in 1964, described an enzyme elaborated by the Actinoplanaceae which was capable of deacylating penicillin antibiotics. Abbott and Fukuda in U.S. Pat. Nos. 4,293,482, 4,299,764, 4,299,762, 4,304,716, and 4,293,490, all issued in 1981, reported that an Actinoplanaceae enzyme was capable of deacylating the A-30912 type of cyclic peptide antibiotic. Reacylation of the A-30912 nucleus to form useful antifungal compounds was reported by Abbott and Fukuda in U.S. Pat. No. 4,287,120, issued in 1981, and in U.S. Pat. Nos. 4,320,052, 4,320,053, 4,320,054 and 4,322,338, issued in 1982; and by Debono in the following U.S. patents issued in 1981: U.S. Pat. Nos. 4,293,483, 4,293,488, 4,293,487, 4,293,485, 4,293,491, 4,293,489, 4,297,277, 4,289,692, 4,293,486 and 4,293,484.

In 1967 Kimura and Tatsuki, in Japanese Patent No. 4058/67 (Derwent Abstr. 26695), described the enzymatic deacylation of the peptide antibiotic glumamycin. The microorganism catalyzing the deacylation was identified as closely related to *Pseudomonas dacunhae*. They stated that "deacylated derivatives of the compounds are useful as the material for synthesis of the related compounds, as in the case of 6-aminopenicillanic acid for penicillin", but gave no examples of re-acylation.

In 1965, Kimura and coworkers reported that a bacterium isolated from soil catalyzed the deacylation of the peptide antibiotic colistin (polymyxin E) (see Kimura, et al., Abstracts of Papers, 21st Meeting of the Pharmaceutical Society of Japan, Tokushima, October, 1965, p. 422). They reported that new derivatives of colistin were prepared by acylation of the deacylated nucleus, but did not discuss whether these derivatives had any activity.

Kato and Shoji [*J. Antibiotics* 29 (12), 1339–1340 (1976)] attempted to use the enzyme described by Kimura et al. to deacylate the cyclic peptide antibiotic octapeptin $C_1$. The enzyme did not catalyze the desired reaction. It was subsequently found that deacylation could be accomplished chemically by oxidation of the β-hydroxyl group of the fatty acid followed by treatment with hydroxylamine.

In 1973 Chihara and coworkers reported their work with colistin. In this work two plant proteases, ficin and papain, were used to hydrolyze colistin to a nonapeptide and a fatty acyl α, γ-diaminobutyric acid residue. The plant enzymes, however, in addition to removing the fatty acid acyl substituent, also removed the terminal amino acid of the colistin molecule [See S. Chihara et al., *Agr. Biol. Chem.* 37 (11), 2455–2463 (1973); ibid. 37 (12), 2709–2717 (1973); ibid. 38 (3), 521–529 (1974); and ibid. 38 (10), 1767–1777 (1974)]. The colistin nonapeptide was isolated and then reacylated with a variety of fatty acid chlorides. Subsequently, Chihara's group produced N-fatty acyl mono-acyl derivatives of colistin nonapeptide. These derivatives restored a tenth amino acid to the colistin nonapeptide and were used to study structure-activity relationships.

The polymyxin antibiotics have been hydrolyzed with the enzyme subtilopeptidase A [See T. Suzuki et al., *J. Biochem.* 56 (4), 335–343 (1964)]. This enzyme deacylated the peptides, but in addition hydrolyzed some of the peptide bonds so that a variety of peptide products resulted.

In 1978 Weber and Perlman reported that a Corynebacterium isolated from soil inactivated the peptide antibiotic amphomycin by deacylation of the isotridecanoic acid side chain [see *J. Antibiotics* 31 (4), 373–374 (1978)].

Kuwana et al. in U.S. Pat. No. 4,050,989, issued in 1977, described the deacylation of pepsininhibiting peptides (pepsidines) by an enzyme from *Bacillus pumilus* and the use of these products to prepare N-acyl-pentapeptide homologs.

Shoji and coworkers deacylated the cyclic peptide antibiotics cerexin A, cerexin B, and brevistin in order to determine the structures of these antibiotics [see J. Shoji and T. Kato, *J. Antibiotics* 28, 764–769 (1975) and ibid. 29 (4), 380–389 (1976); and J. Shoji et al., ibid. 29 (12), 1268–1274 (1976); and ibid. 29 (12), 1275–1280 (1976)]. Deacylation was accomplished with an enzyme preparation prepared from Pseudomonas sp. M-6-3 (polymyxin acylase) and by chemical means. Chemical deacylation, however, resulted in extensive side reactions.

Despite the contributions of these groups, it is extremely difficult, when confronted with the problem of deacylating a peptide antibiotic having a different structure, to know whether an enzyme exists which can be used for this purpose. Finding such an enzyme is even more difficult when the substrate antibiotic contains a cyclic peptide nucleus. Enzymes have a high degree of specificity. Differences in the peptide moiety and in the side chain of the substrate antibiotic will affect the outcome of the deacylation attempt. In addition, many microorganisms make a large number of peptidases which attack different portions of the peptide moiety. This frequently leads to intractable mixtures of products.

Thus, it was most surprising that what may be the same enzyme which was used to deacylate penicillins and the A-30912 antibiotics could also be used successfully to deacylate the A-21978C antibiotics. In each of the A-21978C antibiotics (formula 2), the fatty acid side chain ($R^N$) is attached at the α-amino group of the tryptophan residue. In our co-pending application, entitled "A-21978C CYCLIC PEPTIDES", Ser. No. 380,497 filed May 21, 1982, which is incorporated herein by reference, we describe our discovery that the fatty acid side chain can be cleaved by an enzyme without affecting the chemical integrity of the remainder of the A-21978C peptide.

The enzyme used to effect the deacylation reaction is produced by a microorganism of the family Actinoplanaceae, preferably the microorganism *Actinoplanes utahensis* NRRL 12052, or a variant thereof. To accomplish deacylation, an antibiotic selected from A-21978C complex, A-21978C factors $C_0$, $C_1$, $C_2$, $C_3$, $C_4$, and $C_5$, blocked A-21978C complex, and blocked A-21978C factors $C_0$, $C_1$, $C_2$, $C_3$, $C_4$, and $C_5$ is added to a culture of the microorganism. The terms "blocked A-21978C factors" and "blocked A-21978C complex" refer to individual A-21978C factors or mixtures of factors (complex) wherein the amino group of ornithine and/or kynurenine is blocked with an amino-protecting group. Preferably, the amino-protecting group is located on the δ-amino group of ornithine of the individual factor or mixture of factors. The culture is allowed to incubate with the substrate until the deacylation is substantially complete. The corresponding A-21978C cyclic peptide thereby obtained is separated from the fermentation broth by methods known in the art.

The cyclic peptides obtained by these enzymatic deacylations are shown in formula 3.

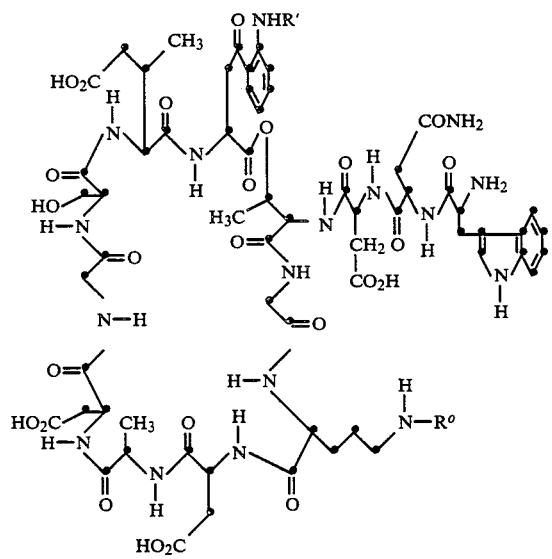

wherein R' and R° are, independently, hydrogen or an amino-protecting group; and the salts thereof.

Removal of the acyl moiety from the A-21978C complex or A-21978C individual factors $C_0$, $C_1$, $C_2$, $C_3$, $C_4$, and $C_5$ gives the compound of formula 3 wherein R' and R° each represent hydrogen, which is the common cyclic peptide present in antibiotic A-21978C factors. For convenience herein, this compound will be called A-21978C nucleus. This compound can also be represented by formula 4:

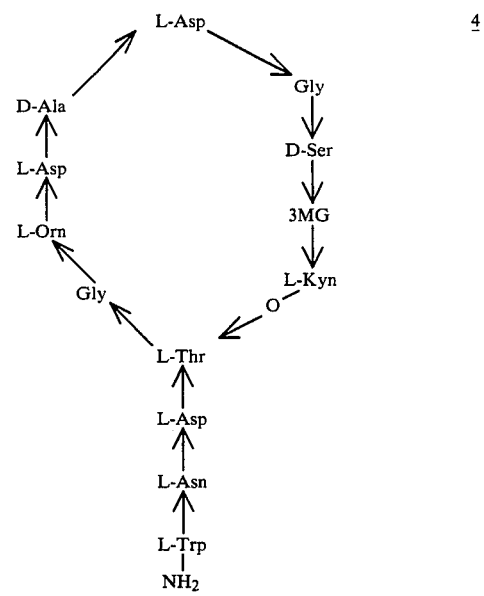

wherein 3MG represents L-threo-3-methylglutamic acid.

The compounds of formula 3 wherein R' or R° are other than hydrogen are prepared by deacylation of appropriately blocked antibiotic A-21978C factors $C_0$, $C_1$, $C_2$, $C_3$, $C_4$ and $C_5$. For convenience herein these compounds will be called blocked A-21978C nuclei. These blocked compounds are useful intermediates to certain peptides of formula 1, i.e. those compounds wherein at least one of $R^1$ and $R^2$ is an amino-protecting group.

As will be apparent to those skilled in the art, A-21978C nucleus and blocked A-21978C nuclei can be obtained either in the form of free amines or of acid addition salts. Although any suitable acid addition salt may be used, those which are non-toxic and pharmaceutically acceptable are preferred.

The method of preparing the A-21978C nuclei of formula 3 from the corresponding A-21978C antibiotic by means of fermentation using *Actinoplanes utahensis* NRRL 12052 is described in our co-pending application Ser. No. 380,497. *A. utahensis* NRRL 12052 is available to the public from the Agricultural Research Culture Collection (NRRL), Northern Regional Research Center, U.S. Department of Agriculture, 1815 North University St., Peoria, Ill. 61604, U.S.A., under the accession number NRRL 12052. Preparation 1 herein illustrates the preparation of A-21978C nucleus by fermentation using the A-21978C complex as the substrate and *Actinoplanes utahensis* NRRL 12052 as the microorganism.

Other Actinoplanaceae cultures which can be used to prepare the A-21978C nuclei of formula 3 are available to the public from the Northern Regional Research Laboratory under the following accession numbers:

| | |
|---|---|
| *Actinoplanes utahensis* | NRRL 12052 |
| *Actinoplanes missouriensis* | NRRL 12053 |

| -continued | |
|---|---|
| Actinoplanes sp. | NRRL 8122 |
| Actinoplanes sp. | NRRL 12065 |
| Streptosporangium roseum var. hollandensis | NRRL 12064 |

The effectiveness of any given strain of microorganism within the family Actinoplanaceae for carrying out the deacylation is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Micrococcus luteus* assay. Loss of antibiotic activity is an indication that the microorganism produces the requisite enzyme for deacylation. This must be verified, however, using one of the following methods: (1) analysis by HPLC for presence of the intact nucleus; or (2) re-acylation with an appropriate side chain (e.g. lauroyl, n-decanoyl or n-dodecanoyl) to restore activity.

The present invention relates to novel compounds derived by acylating an A-21978C nucleus (compound of formula (3), an A-21978C factor or a blocked A-21978C factor. The compounds of the present invention have the chemical structure depicted in formula 1:

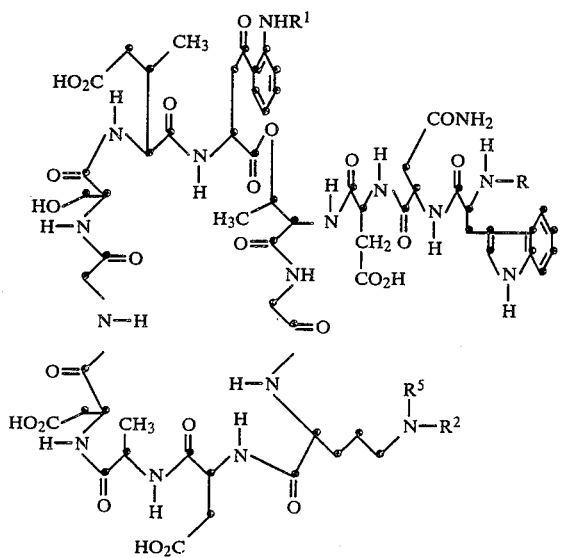

in which R, $R^1$ and $R^2$ are, independently, hydrogen, $C_4$–$C_{14}$-alkyl, optionally substituted $C_2$–$C_{19}$-alkanoyl, $C_5$–$C_{19}$-alkenoyl or an amino-protecting group; $R^3$, $R^4$ and $R^5$ are hydrogen or (i) $R^3$ and $R^1$ and/or (ii) $R^4$ and R and/or (iii) $R^5$ and $R^2$, taken together, may represent a $C_4$–$C_{14}$ alkylidene group; provided that (1) at least one of R, $R^1$ or $R^2$ must be other than hydrogen or an amino-protecting group, (2) at least one of $R^1$ or $R^2$ must be hydrogen or an amino-protecting group, (3) the R, $R^1$ and $R^2$ groups must together contain at least four carbon atoms, and (4) when $R^1$ and $R^2$ are both selected from hydrogen or an amino-protecting group, R cannot be 8-methyldecanoyl, 10-methyldodecanoyl, 10-methylundecanoyl, the mixed $C_{10}$-alkanoyl group of A-21978$C_0$ or the specific $C_{12}$-alkanoyl groups of A-21978C factors $C_4$ and $C_5$; and the salts thereof.

The term "$C_4$–$C_{14}$-alkylidenyl" refers to a group of the formula

wherein $R^3$ and $R^4$ are hydrogen or an alkyl group of from 3 to 13 carbon atoms, provided that one of $R^3$ and $R^4$ must be other than hydrogen and further provided that the sum of the carbon atoms in $R^3$ and $R^4$ must be no greater than 13. Those compounds wherein one of R, $R^1$ or $R^2$ is $C_4$–$C_{14}$-alkylidenyl are known as Schiff's bases.

The term "$C_4$–$C_{14}$-alkyl" refers to a univalent saturated, straight- or branched-chain alkyl group containing from 4 to 14 carbon atoms. Those compounds wherein one of R, $R^1$ or $R^2$ are $C_4$–$C_{14}$-alkyl, referred to herein as "reduced Schiff's bases", are prepared by reduction of the corresponding compounds where R and $R^4$, $R^1$ and $R^3$ or $R^2$ and $R^5$ represent a $C_4$–$C_{14}$-alkylidenyl group.

The terms "optionally substituted $C_2$–$C_{19}$-alkanoyl" and "$C_5$–$C_{19}$-alkenoyl" refer to acyl groups derived from carboxylic acids containing from 2 to 19 and 5 to 19 carbon atoms, respectively. When the R group is alkanoyl, the alkyl portion is a univalent saturated, straight-chain or branched-chain hydrocarbon radical which can optionally bear one hydroxyl, carboxyl, or $C_1$–$C_3$-alkoxy group or from one to three halo substituents selected from chlorine, bromide, and fluorine. When R is alkenoyl, the alkenyl portion is a univalent, unsaturated, straight-chain or branched-chain hydrocarbon radical containing not more than three double bonds. The double bond portion(s) of the unsaturated hydrocarbon chain may be either in the cis or trans configuration.

The term "amino-protecting group" refers to a recognized amino-protecting group which is compatible with the other functional groups in the A-21978C molecule. Preferably, amino-protecting groups are those which can be readily removed from the subsequently acylated compound. Examples of suitable protecting groups can be found in "Protective Groups in Organic Synthesis" by Theodora W. Greene, John Wiley and Sons, New York, 1981, chapter 7. Especially preferable amino-protecting groups are the tert-butoxycarbonyl and benzyloxycarbonyl groups.

In subgeneric aspects, the invention contemplates the following preferred enbodiments of the compounds of formula 1:

(a) The compounds wherein R is alkanoyl of the formula

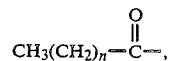

wherein n is an integer from 3 to 17;

(b) The compounds wherein R is alkanoyl of the formula

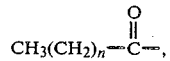

wherein n is 5 to 14;

(c) The compounds wherein R is alkanoyl of the formula

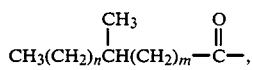

wherein n and m are each, independently, an integer from 0 to 14, provided that n+m must be no less than 1 and no greater than 15; and further provided that, when n is 0, m cannot be 8 and, when n is 1, m cannot be 6 or 8;

(d) The compounds wherein R is cis or trans alkenyl of the formula

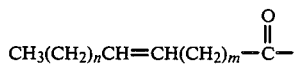

wherein n and m are each, independently, an integer from 0 to 14, provided that n+m must be no less than 1 and no greater than 15;

(e) The compounds wherein R is cis or trans alkenyl of the formula

wherein n is an integer of from 4 to 15;

(f) The compounds wherein R is alkyl of the formula $CH_3(CH_2)_n$— and n is an integer from 5 to 12; and (g) The compounds wherein R is:

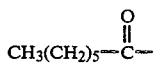

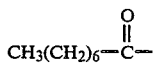

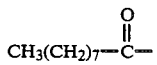

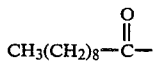

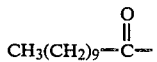

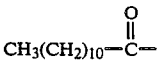

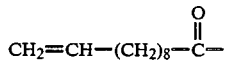

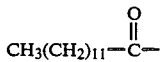

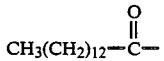

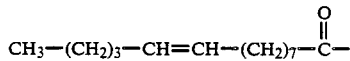

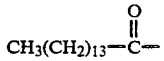

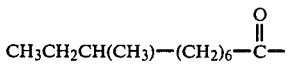

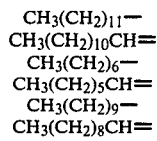

The compounds of formula 1 are capable of forming salts. These salts are also part of this invention. Such salts are useful, for example, for separating and purifying the compounds. Pharmaceutically-acceptable alkali-metal, alkaline-earth-metal, amine and acid-addition salts are particularly useful.

For example, the compounds of formula 1 have four free carboxyl groups which can form salts. Partial, mixed and complete salts of these carboxyl groups are, therefore, contemplated as part of this invention. In preparing these salts, pH levels greater than 10 should be avoided due to the instability of the compounds at such levels.

Representative and suitable alkali-metal and alkaline-earth metal salts of the compounds of formula 1 include the sodium, potassium, lithium, cesium, rubidium, barium, calcium and magnesium salts. Suitable amine salts of the formula 1 compounds include the ammonium and the primary, secondary, and tertiary $C_1$–$C_4$-alkylammonium and hydroxy-$C_2$–$C_4$-alkylammonium salts. Illustrative amine salts include those formed by reaction of a formula 1 compound with ammonium hydroxide, methylamine, sec-butylamine, isopropylamine, diethylamine, di-isopropylamine, cyclohexylamine, ethanolamine, triethylamine, 3-amino-1-propanol and the like.

The alkali-metal and alkaline-earth-metal cationic salts of the compounds of formula 1 are prepared according to procedures commonly used for the preparation of cationic salts. For example, the free acid form of a formula 1 compound is dissolved in a suitable solvent such as warm methanol or ethanol; a solution containing the stoichiometric quantity of the desired inorganic base in aqueous methanol is added to this solution. The salt thus formed can be isolated by routine methods, such as filtration or evaporation of the solvent. A convenient method of preparing salts is by the use of ion-exchange resins.

The salts formed with organic amines can be prepared in a similar manner. For example, the gaseous or liquid amine can be added to a solution of a formula 1 compound in a suitable solvent such as ethanol; the solvent and excess amine can be removed by evaporation.

The compounds of this invention also have free amino groups and can, therefore, form acid addition salts. Such salts are also part of this invention. Representative and suitable acid-addition salts of the compounds of formula 1 include those salts formed by standard reaction with both organic and inorganic acids such as, for example, hydrochloric, sulfuric, phosphoric, acetic, succinic, citric, lactic, maleic, fumaric, palmitic, cholic, pamoic, mucic, D-glutamic, d-camphoric, glutaric, glycolic, phthalic, tartaric, lauric, stearic, salicylic, methanesulfonic, benzenesulfonic, sorbic, picric, benzoic, cinnamic and like acids.

The compounds of formula 1 wherein R, $R^1$ or $R^2$ are alkanoyl, alkenoyl or an amino-protecting group are prepared by acylating an A-21978C factor, a blocked A-21978C factor, a compound of formula 3 or an appropriate compound of formula 3 which is blocked at the α-amino group of tryptophan with the desired alkanoyl or alkenoyl side chain, using methods conventional in the art for forming an amide bond. The acylation is accomplished, in general, by reacting the selected compound with an activated derivative of the alkanoic acid or alkenoic acid corresponding to the desired acyl side chain group (R, $R^1$ or $R^2$). The term "activated derivative" means a derivative which renders the carboxyl function of the acylating agent reactive to coupling with the primary amino group to form the amide bond which links the acyl side chain to the nucleus. Suitable activated derivatives, their methods of preparation, and their methods of use as acylating agents for a primary amine will be recognized by those skilled in the art. Preferred activated derivatives are: (a) an acid halide (e.g. an acid chloride), (b) an acid anhydride (e.g. an alkoxyformic acid anhydride) or (c) an activated ester (e.g. a 2,4,5-trichlorophenyl ester). Other methods for activating the carboxyl function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

It will be recognized by those skilled in the art that the compounds of formula 1 are prepared using selective acylation procedures and with the assistance of amino-protecting groups. For example, when a compound of formula 3 wherein R' and R° are hydrogen is the starting material, acylation can occur at both the α-amino group of tryptophan and the δ-amino group of ornithine to give $N_{Trp}$, $N_{Orn}$-diacyl derivatives. To obtain derivatives monoacylated at the α-amino group of tryptophan, therefore, it is preferable to acylate a compound of formula 3 wherein the δ-amino group of ornithine (the R° position) is blocked by an amino-protecting group. Such starting materials are preferably obtained by blocking the A-21978C factor at this position before it is deacylated. The aromatic amino group of kynurenine is the least reactive of the three free amino groups in the A-21978C nucleus. Thus, acylation at kynurenine involves appropriate blocking of the amino groups of tryptophan and ornithine, but acylation at R or $R^1$ does not usually involve blocking the amino group of kynurenine.

Schemes I, II, and III outline general procedures for the preparation of the compounds of formula 1 wherein one of R, $R^1$ or $R^2$ is alkanoyl, alkenoyl, or an amino-protecting group. In these Schemes the following symbols are used:
[*] = remainder of A-21978C
$N_T$ = α-amino group of tryptophan
$N_O$ = δ-amino group of ornithine
$N_K$ = aromatic amino group of kynurenine
R, $R^1$, $R^2$ = substituents as defined
$R_N$ = acyl group of natural factor
B, $B^1$ = amino-protecting groups
Acyl = an acylation step
Deacyl = a deacylation step
Block = acylation with an amino-protecting group
Deblock = removal of an amino-protecting group In Scheme I the $N_{Trp}$-monoacyl derivatives of A-21978C are represented by general formula 3 and the $N_{Trp}$, $N_{Orn}$-diacyl derivatives of A-21978C are represented by general formula 4. Those $N_{Trp}$, $N_{Orn}$-diacyl derivatives wherein the $N_{Trp}$-acyl group is that of a natural A-21978C factor are represented by general formula 8.

Scheme I:
Preparation of $N_{Trp}$—Monoacyl and $N_{Trp}$, $N_{Orn}$—Diacyl-A21978C Derivatives

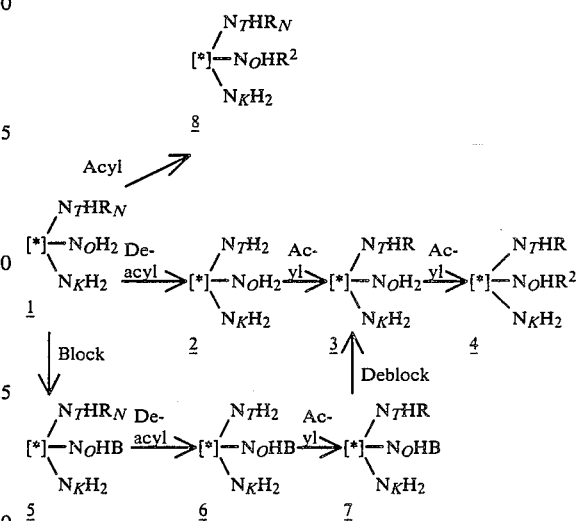

In Scheme II the $N_{Trp}$, $N_{Kyn}$-diacyl derivatives of A-21978C are represented by general formula 10. Those $N_{Trp}$, $N_{Kyn}$-diacyl derivatives wherein the $N_{Trp}$-acyl group is that of a natural A-21978C factor are represented by general formula 12. The compounds having general formulas 5, 6 and 7 are also described in Scheme I.

Scheme II:
Preparation of $N_{Trp}$, $N_{Kyn}$—Diacyl-A-21978C Derivatives

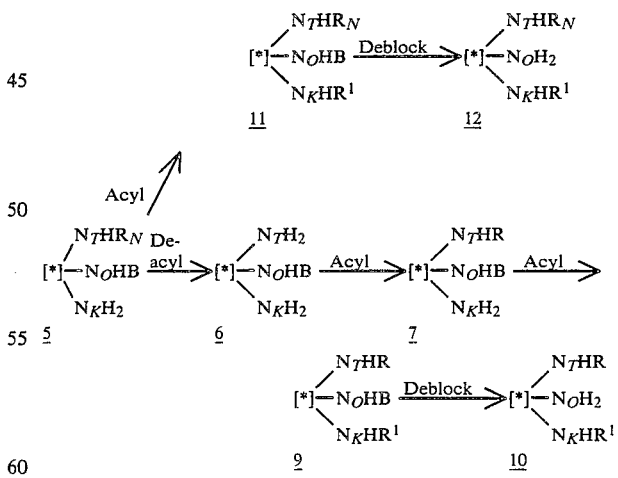

In Scheme III the $N_{Orn}$-monoacyl derivatives of A-21978C are represented by general formula 18, the $N_{Kyn}$-monoacyl derivatives of A-21978C are represented by general formula 15, and the $N_{Orn}$, $N_{Kyn}$-diacyl derivatives of A-21978C are represented by general formula 20. The compounds having general formula 6 are also described in Schemes I and II.

Scheme III:
Preparation of $N_{Orn}$—Monoacyl, $N_{Kyn}$—Monoacyl and $N_{Orn}$, $N_{Kyn}$—Diacyl-A-21978C Derivatives

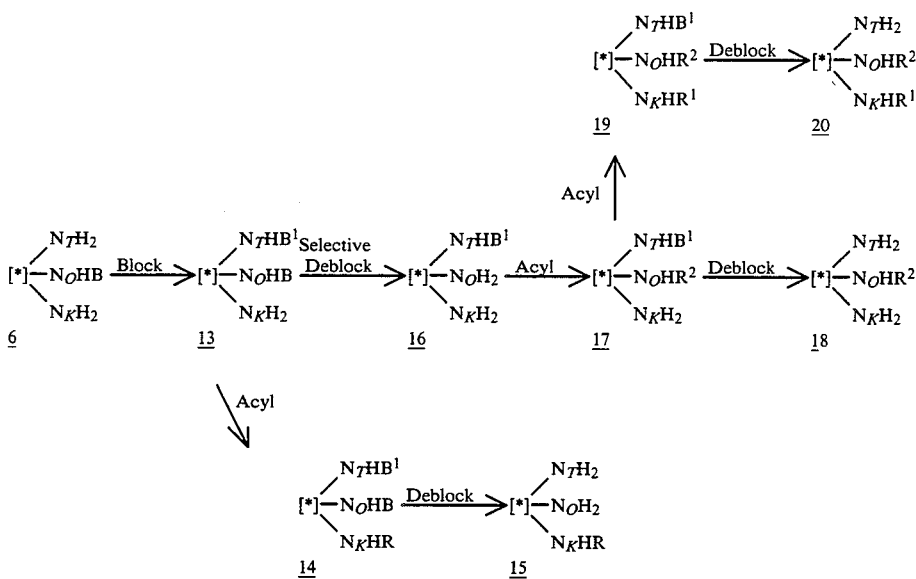

The compounds of formula 1 in which one or more of the amino groups are substituted by an alkylidenyl (the Schiff's bases) or alkyl group (the reduced Schiff's bases) can be prepared by known methods for preparing Schiff's bases and reducing such bases, respectively. Thus, the Schiff's bases are prepared by reaction (condensation) of the primary amino group of tryptophan, ornithine or kynurenine of A-21978C with an appropriate aldehyde or ketone in a suitable solvent. Reduction of the imine bond of the Schiff's base, to obtain the corresponding formula 1 compound in which R, $R^1$ or $R^2$ is alkyl, can be accomplished by known selective reduction procedures. A preferred reducing agent for this reaction is sodium cyanoborohydride.

Under the in vitro test conditions used, the Schiff's bases do not show antibacterial activity, possibly due to their instability in the assay medium. They are useful, however, as intermediates to the reduced Schiff's bases. When the Schiff's base is used as an intermediate, it is not necessary to isolate the intermediate prior to reducing it to form the reduced Schiff's base.

A preferred method for preparing the compounds of formula 1 in which one of R, $R^1$ or $R^2$ is alkanoyl or alkenoyl is by the active ester method. The compound of formula 3 wherein R'=H and R°=t-BOC, i.e. the A-21978C $N_{Orn}$-t-BOC nucleus or "tBOC nucleus", is an especially preferred starting material in the preparation of formula 1 compounds. The 2,4,5-trichlorophenyl ester of the desired alkanoic or alkenoic acid is a preferred acylating agent. In this method, an excess amount of the active ester is reacted with the t-BOC nucleus at room temperature in a non-reactive organic solvent such as DMF, THF, diethyl ether or dichloromethane. The reaction time is not critical, although a time of about 6 to about 20 hours is preferred. At the conclusion of the reaction, the solvent is removed, and the residue is purified. A particularly useful purification method is reversed-phase HPLC, using LP-1/$C_{18}$ as the stationary phase and a mixture of $H_2O/CH_3OH/CH_3CN$/pyridine/HOAc as the solvent system. The t-BOC group is removed by treatment with trifluoroacetic acid/anisole/triethylsilane or, preferably, trifluoroacetic acid/1,2-ethanedithiol for from about three to about five minutes at room temperature. After the solvent is removed, the residue is purified by reversed-phase HPLC.

An alternative acylation method is a modified Schotten-Baumann procedure in which the unblocked nucleus is treated with the acid chloride of the desired alkanoic acid or alkenoic acid in a pyridine/water mixture. In this method, an excess of the acid chloride in a non-reactive organic solvent (such as acetone) is added slowly to a solution of the nucleus in 90% pyridine/10% water (by volume). The unreacted acid chloride is separated from the reaction product by extraction into an immiscible organic solvent (e.g., diethyl ether). Final purification is by reversed-phase HPLC, as previously described.

The alkanoic and alkenoic acids used as starting materials for the acylation reaction, and the activated derivatives thereof (in particular, the acid chlorides and the 2,4,5-trichlorophenyl esters), are known compounds or can be prepared from known compounds by known methods. The 2,4,5-trichlorophenyl esters are conveniently made by treating the acid chloride of the alkanoic or alkenoic acid with 2,4,5-trichlorophenol in the presence of pyridine or by treating the free alkanoic or alkenoic acid with 2,4,5-trichlorophenol in the presence of N,N'-dicyclohexylcarbodiimide as a coupling agent. The 2,4,5-trichlorophenyl ester derivative can be purified by column chromatography over silica gel.

When an A-21978C cyclic peptide of this invention is used as an antibacterial agent, it may be administered either orally or parenterally. As will be appreciated by those skilled in the art, the A-21978C compound is commonly administered together with a pharmaceutically acceptable carrier or diluent. The dosage of A-21978C compound will depend upon a variety of considerations, such as, for example, the nature and severity of the particular infection to be treated. Those skilled in the art will recognize that appropriate dosage ranges and/or dosage units for administration may be determined by considering the MIC and ED$_{50}$ values and toxicity data herein provided together with factors such as pharmacokinetics, the patient or host and the infecting microorganism.

The methods of making and using the compounds of the present invention are illustrated in the following examples:

PREPARATION 1

Preparation of A-21978C Nucleus

A. Fermentation of *Actinoplanes utahensis*

A stock culture of *Actinoplanes utahensis* NRRL 12052 is prepared and maintained on an agar slant. The medium used to prepare the slant is selected from one of the following:

| Ingredient | Amount |
|---|---|
| MEDIUM A | |
| Pre-cooked oatmeal | 60.0 g |
| Yeast | 2.5 g |
| K$_2$HPO$_4$ | 1.0 g |
| Czapek's mineral stock* | 5.0 ml |
| Agar | 25.0 g |
| Deionized water | q.s. to 1 liter | pH before autoclaving is about 5.9; adjust to pH 7.2 by addition of NaOH; after autoclaving, pH is about 6.7.
*Czapek's mineral stock has the following composition:

| | |
|---|---|
| FeSO$_4$.7H$_2$O (dissolved in 2 ml conc HCl) | 2 g |
| KCl | 100 g |
| MgSO$_4$.7H$_2$O | 100 g |
| Deionized water | q.s. to 1 liter |
| MEDIUM B | |
| Potato dextrin | 5.0 g |
| Yeast extract | 0.5 g |
| Enzymatic hydrolysate of casein* | 3.0 g |
| Beef extract | 0.5 g |
| Glucose | 12.5 g |
| Corn starch | 5.0 g |
| Meat peptone | 5.0 g |
| Blackstrap molasses | 2.5 g |
| MgSO$_4$.7H$_2$O | 0.25 g |
| CaCO$_3$ | 1.0 g |
| Czapek's mineral stock | 2.0 ml |
| Agar | 20.0 g |
| Deionized water | q.s. to 1 liter |

*N—Z—Amine A, Humko Sheffield Chemical, Lyndhurst, NJ.

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
|---|---|
| Pre-cooked oatmeal | 20.0 g |
| Sucrose | 20.0 g |
| Yeast | 2.5 g |
| Distiller's Dried Grain* | 5.0 g |
| K$_2$HPO$_4$ | 1.0 g |
| Czapek's mineral stock | 5.0 ml |
| Deionized water | q.s. to 1 |
| Adjust to pH 7.4 with NaOH; after autoclaving, pH is about 6.8. | |

*National Distillers Products Co., 99 Park Ave., New York, NY.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen, *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (80 ml), prepared as above-described, is used to inoculate 10 liters of sterile production medium selected from one of the following:

| MEDIUM I | |
|---|---|
| Ingredient | Amount (g/L) |
| Peanut meal | 10.0 |
| Soluble meat peptone | 5.0 |
| Sucrose | 20.0 |
| KH$_2$PO$_4$ | 0.5 |
| K$_2$HPO$_4$ | 1.2 |
| MgSO$_4$.7H$_2$O | 0.25 |
| Tap water | q.s. to 1 liter |

The pH of the medium is about 6.9 after sterilization by autoclaving at 121° C. for 45 minutes at about 16–18 psi.

| MEDIUM II | |
|---|---|
| Ingredient | Amount (g/L) |
| Sucrose | 30.0 |
| Peptone | 5.0 |
| K$_2$HPO$_4$ | 1.0 |
| KCl | 0.5 |
| MgSO$_4$.7H$_2$O | 0.5 |
| FeSO$_4$.7H$_2$O | 0.002 |
| Deionized water | q.s. to 1 liter |

Adjust to pH 7.0 with HCl; after autoclaving, pH is about 7.0.

| MEDIUM III | |
|---|---|
| Ingredient | Amount (g/L) |
| Glucose | 20.0 |
| NH$_4$Cl | 3.0 |
| Na$_2$SO$_4$ | 2.0 |
| ZnCl$_2$ | 0.019 |
| MgCl$_2$.6H$_2$O | 0.304 |
| FeCl$_3$.6H$_2$O | 0.062 |
| MnCl$_2$.4H$_2$O | 0.035 |
| CuCl$_2$.2H$_2$O | 0.005 |
| CaCO$_3$ | 6.0 |

| MEDIUM III | |
| --- | --- |
| Ingredient | Amount (g/L) |
| $KH_2PO_4$* | 0.67 |
| Tap water | q.s. to 1 liter |

*Sterilized separately and added aseptically. Final pH about 6.6.

The inoculated production medium is allowed to ferment in a 14-liter fermentation vessel at a temperature of about 30° C. for about 66 hours. The fermentation medium is stirred with conventional agitators at about 600 RPM and aerated with sterile air to maintain the dissolved oxygen level above 30% of air saturation at atmospheric pressure.

B. Deacylation of A-21978C

A fermentation of *A. utahensis* is carried out as described in Section A, using slant medium A and production medium I and incubating the production medium for about 67 hours. Crude A-21978C complex (100 g), prepared as described in U.S. Pat. No. 4,208,403, is added to the fermentation medium.

Deacylation of the A-21978C complex is monitored by assay against *Micrococcus luteus*. The fermentation is allowed to continue until deacylation is complete as indicated by disappearance of activity vs. *M. luteus*, a period of about 24 hours.

C. Isolation of A-21978C Nucleus

Whole fermentation broth (20 liters), obtained as described in Section B, was filtered with a filter aid (Hyflo Super-Cel, Johns Manville Corp.). The mycelial cake was discarded. The filtrate thus obtained was passed through a column containing 1.5 liters of HP-20 resin (DIAION High Porous Polymer HP-Series, Mitsubishi Chemical Industries Limited, Tokyo, Japan). The effluent thus obtained was discarded. The column was then washed with deionized water (10 L.) to remove residual filtered broth. This wash water was discarded. The column was then eluted with water:acetonitrile mixtures (10 L. each of 95:5, 9:1, and 4:1), collecting 1-liter fractions.

Elution was monitored by paper chromatography, using an n-butanol:pyridine:acetic acid:water (15:10:3:12) solvent system and detecting compounds by UV fluorescence. In this system the A21978C factors have an $R_f$ value of about 0.56 and A-21978C nucleus has an $R_f$ value of about 0.32. The product can also be checked by analytical HPLC, using silica gel/$C_{18}$ and a solvent system of water:methanol (3:1) containing 0.1% ammonium acetate, detecting the nucleus with a UV monitor at 254 nm.

Fractions containing the nucleus were combined, concentrated under vacuum to remove the acetonitrile and freeze-dried to give 40.6 g of semi-purified A-21978C nucleus.

D. Purification of A-21978C Nucleus

Semi-purified A-21978C nucleus (15 g), obtained as described in Section C, was dissolved in 75 ml of water:methanol:acetonitrile (82:10:8) containing 0.2% acetic acid and 0.8% pyridine. This solution was pumped onto a 4.7-×192-cm column containing 3.33 L. of silica gel/$C_{18}$ (Quantum LP-1, Quantum Industries, 341 Kaplan Drive, Fairfield, NJ 07006). The column was developed with the same solvent system. Fractions having a volume of 350 ml were collected. Separation was monitored at 280 nm with a UV monitor. Fractions containing the nucleus were combined, concentrated under vacuum to remove solvents and freeze-dried to give 5.2 g of purified A-21978C nucleus.

E. Characteristics of A-21978C Nucleus

A-21978C nucleus has the following characteristics:
(a) Form: white amorphous solid which fluoresces under short-wave UV
(b) Empirical formula: $C_{62}H_{83}N_{17}O_{25}$
(c) Molecular weight: 1465
(d) Solubility: soluble in water
(e) Infrared absorption spectrum (KBr disc) shows absorption maxima at the following frequencies ($cm^{-1}$): 3300 (broad), 3042 (weak), 2909 (weak), 1655 (strong), 1530 (strong), 1451 (weak), 1399 (medium), 1222 (medium), 1165 (weak), 1063 (weak) and 758 (medium to weak)
(f) UV absorption spectrum in methanol shows maxima at 223 nm ($\epsilon$ 41,482) and 260 nm ($\epsilon$ 8,687)
(g) Electrometric titration in 66% aqueous dimethylformamide indicates the presence of four titratable groups with $pK_a$ values of about 5.2, 6.7, 8.5 and 11.1 (initial pH 6.12)

PREPARATION 2

Alternate Preparation of A-21978C Nucleus

A-21978C nucleus was prepared according to the method of Preparation 1 except for certain changes in Section B. The A. utahensis culture was incubated initially for about 48 hours; the substrate was semi-purified A-21978C complex (50 g); and incubation after addition of the substrate was about 16 hours. The broth filtrate was passed over a column containing 3.1 liters of HP-20 resin. The column was washed with 10 volumes of water and then was eluted with water:acetonitrile (95:5). Elution was monitored as in Preparation 1. After collecting 24 liters, the eluting solvent was changed to water:acetonitrile (9:1). Fractions containing the nucleus were eluted with this solvent. These fractions were combined, concentrated under vacuum to remove acetonitrile, and freeze-dried to give 24.3 g of semi-purified A-21978C nucleus.

This semi-purified A-21978C nucleus (24.3 g) was dissolved in water (400 ml). The solution was pumped onto a 4.7-×192-cm steel column containing 3.33 liters of silica gel (Quantum LP-1/$C_{18}$) prepared in water:methanol:acetonitrile (8:1:1) containing 0.2% acetic acid and 0.8% pyridine. The column was developed with the same solvent at a pressure of about 2000 psi, collecting 350 ml fractions. Elution was monitored by UV at 280 nm. Fractions containing the nucleus were combined, concentrated under vacuum to remove solvents, and freeze-dried to give 14 g of highly purified A-21978C nucleus.

PREPARATION 3

Preparation of $N_{Orn}$-t-BOC A-21978C Factors $C_2$ and $C_3$

A mixture of A-21978C factors $C_2$ and $C_3$ (10 g), prepared as described in U.S. Pat. No. 4,208,403, was dissolved in water (50 ml) with sonication (200 mg/ml). The pH of the solution was adjusted from 4.05 to 9.5 with 5N NaOH (3.6 ml). Di-tert-butyl dicarbonate (3.0 ml) was added, and the reaction mixture was stirred at room temperature for 2 hours. The pH of the reaction was maintained at 9.5 by manual addition of 5N NaOH (6.5 ml added in 2 hours).

The reaction was monitored periodically by TLC on silica gel, using $CH_3CN:H_2O$ (7:3 and 8:2) solvent systems and detecting by UV.

After about 10 minutes the reaction solution became rapidly turbid, and base consumption increased. After 30 minutes, the rate of increase in turbidity and the rate of base consumption decreased, indicating that the reaction was complete. Nevertheless, the reaction was continued for an additional 90 minutes to insure completion. At the end of the two-hour reaction, the reaction material was lyophilized immediately to give 12.7 g of $N_{Orn}$-t-BOC-A-21978 factors $C_2$ and $C_3$.

Using similar procedures, two 10-g reactions and a 30-g reaction were run. In each of these the reaction time was only 40 minutes. The two 10-g experiments gave 11.9 and 12.1 g of product, respectively. The 30-g reaction gave 35.4 g of product.

PREPARATION 4

Preparation of A-21978C $N_{Orn}$-t-BOC Nucleus

A. Fermentation of *A. utahensis*

A fermentation of *A. utahensis was carried out as described in Preparation* 1, Section A, using slant medium A and production medium I and incubating the production medium for about 66 hours.

B. Deacylation of $N_{Orn}$-t-BOC Complex

The A-21978C $N_{Orn-t-BOC\ complex}$ (1185 g of crude substrate which contained about 176 g of A-21978C complex) was added to the fermentation medium. Deacylation was carried out as described in Preparation 1, Section B. Deacylation was complete, as indicated by HPLC, after about 24 hours.

C. Isolation of A-21978C $N_{Orn}$-t-BOC Nucleus

Fermentation broth (100 L.), obtained as described in Section B, was filtered with a filter aid (Hyflo Supercel). The filtrate was passed over a column containing 7.5 L. of HP-20 resin (DIAION); the column was washed with water (38 L.). Elution was monitored by silica gel/$C_{18}$ HPLC with UV detection at 254 nm. Some nucleus was eluted in the wash. Subsequent elution of nucleus was carried out with water:acetonitrile mixtures as follows: (95:5)-40 L.; (9:1)-40 L.; and (85:15)-100 L. Fractions containing the nucleus were combined, concentrated under vacuum to remove solvent, and freeze-dried to give 298.5 g of semi-purified A-21978C $N_{Orn-t-BOC\ nucleus}$.

D. Purification of A-21978C $N_{Orn}$-t-BOC Nucleus

Semi-purified A-21978C $N_{Orn}$-t-BOC nucleus (30 g), obtained as described in Section C, was dissolved in water:acetonitrile (9:1) containing 0.2% acetic acid and 0.8% pyridine (75 ml). This solution was applied to a 4.7-×192-cm steel column containing 3.33 L. of silica gel (Quantum LP-1/$C_{18}$) equilibrated in the same solvent system. The column was developed under pressure with water:acetonitrile:methanol (80:15:5) containing 0.2% acetic acid and 0.8% pyridine, collecting 350-ml fractions and detecting product by UV at 280 nm. Fractions containing the product were combined, concentrated under vacuum to remove solvent and freeze-dried to give 18.4 g of purified A-21978C $N_{Orn}$-t-BOC nucleus.

A-21978C t-BOC nucleus has the following characteristics:
(a) Form: white amorphous solid which fluoresces under short-wave UV
(b) Empirical formula: $C_{67}H_{91}N_{17}O_{27}$
(c) Molecular weight: 1565
(d) Solubility: soluble in water
(e) Infrared absorption spectrum (KBr disc) shows absorption maxima at the following frequencies ($cm^{-1}$): 3345 (broad), 3065 (weak), 2975 (weak), 2936 (weak), ~1710 (shoulder), 1660 (strong), 1530 (strong), 1452 (weak), 1395 (medium), 1368 (weak), 1341 (weak), 1250 (medium), 1228 (medium), 1166 (medium to weak) and 1063 (weak)
(f) UV absorption spectrum in 90% ethanol shows maxima at: 220 nm ($\epsilon$ 42,000) and 260 nm ($\epsilon$ 10,600)
(g) HPLC retention time=6min. on 4.6-×300-mm silica-gel $C_{18}$ column, using $H_2O/CH_3CN/CH_3OH$ (80:15:5) solvent containing 0.2% $NH_4OAc$ at a flow rate of 2 ml/min with UV detection

PREPARATION 5

Alternative Purification of A-21978C $N_{Orn}$-t-BOC Nucleus

Semi-purified A-21978C $N_{Orn}$-t-BOC nucleus (10.8 g), obtained as described in Preparation 4, Section C, was dissolved in water and applied to a column containing 80 ml of Amberlite IRA-68 (Rohm and Haas, Philadelphia, PA, acetate cycle). The column was washed with water and, at a flow rate of 5 ml/min, was eluted sequentially with 0.05N acetic acid (1080 ml), 0.1N acetic acid (840 ml), and 0.2N acetic acid (3120 ml), collecting 120-ml fractions. The column was monitored with analytical HPLC over silica gel/$C_{18}$, using a system of water:acetonitrile:methanol (80:15:5) containing 0.2% ammonium acetate and detecting product with UV at 254 nm. Fractions containing the product were combined; the pH of the solution was adjusted to 5.8 with pyridine; the resulting solution was concentrated under vacuum to a volume of about 200 ml. Water was added to the concentrate, and the resulting solution was reconcentrated to remove pyridine. This concentrate was freeze-dried to give 3.46 g of purified A-21978C $N_{Orn}$-t-BOC nucleus.

EXAMPLES 1–16

The preparation of various alkanoyl and alkenoyl derivatives by acylation of formula 3 compounds, representative of the preparation of the compounds of formula 1, is shown in Table I, below. The derivatives in Table I are made either by the modified Schotten-Bauman reaction using an acid chloride as the acylating agent (Method A) or by the active ester method using the 2,4,5-trichlorophenyl ester as the acylating agent (Method B). The general procedures for carrying out the acylation reactions by Method A or Method B are set forth below:

Method A (Modified Schotten-Bauman Reaction)

This method involves reaction of a formula 3 nucleus with the alkanoic or alkenoic acid chloride that corresponds to the desired acyl side chain.

A formula 3 compound (1.95–2.16 g, 1.33–1.47 mmoles) or a formula 2 compound (409 mg, 0.25 mmole) is dissolved in 200 ml of pyridine/$H_2O$ (9:1). The acylating agent (18–20 mmoles excess acyl chloride dissolved in 15 ml acetone) is added dropwise over 1–3 hours, and the reaction is stirred at ambient temperature for an additional 2-3 hours. The reaction mixture is concentrated to remove the acetone. The aqueous phase which remains is diluted to a volume of about 200 ml with water. The pH of this solution is adjusted to pH 3.0 to 3.5 with glacial acetic acid. This solution is washed 8 times with equal volumes of diethyl ether and then is lyophilized.

The crude acylated derivative is purified by reversed-phase HPLC as follows: The sample, dissolved in water or the eluant system (about 4-6.5 ml), is injected into a 33-×⅜-inch stainless-steel column, packed with $LP_1/C_{18}$ support. The column is eluted with a solvent system consisting of $H_2O:MeOH:CH_3CN$:pyridine:-HOAC. Elution is performed at a pressure of about 1500-2000 psi with a flow rate of about 10-12 ml/min, using an LDC duplex pump (Milton-Roy). Effluent is monitored by UV detection, using an ISCO-UA-5 detector at 280 nm. The desired fractions are combined and evaporated to dryness in vacuo to yield the desired alkanoyl derivative. The purified product is analyzed by TLC using reversed-phase plates (Whatman $KC_{18}$) and a $H_2O:MeOH:CH_3CN$:pyridine:HOAc (45:15:40:2:2) solvent system. The plates are observed under UV light to detect the product. The products are also analyzed by UV (extinction coefficients at 220 nm and 260 nm) and by amino acid analysis. Purity is determined by analytical reversed-phase HPLC ($C_{18}$ Microbondapak, Waters Co.) with a $H_2O:MeOH:CH_3CN$:pyridine:HOAc solvent system, monitoring eluent with UV at 280 nm.

Method B (2,4,5-Trichlorophenyl Active Ester Method)

A solution of $N_{Orn}$-t-BOC A-21978C nucleus (1.0 g, 0.64 mmol), A-21978C nucleus (0.5-1.0 g, 0.34-0.68 mmole), or A-21978C, (946 mg, 0.58 mmole) and a 3.5 molar excess of trichlorophenyl-acyl active ester are dissolved in DMF (100 ml) and stirred at from about room temperature to about 50° C. for from about 6 to about 20 hours. The reaction mixture is concentrated to an oil in vacuo. The oil is triturated with 50 ml $Et_2O$:toluene (1:1) and washed with $Et_2O$. The monoacylated and di-acylated A-21978C nucleus derivatives, acylated A-21978C₁, and acylated t-BOC A-21978C nucleus are purified as described in Method A.

The acylated t-BOC-A-21978C nucleus is deblocked using 50 mg/ml of trifluoroacetic acid:anisole:triethylsilane (10:1:1) at from about $-10°$ to about $-0°$ C. for 3-5 minutes. This reaction mixture is concentrated in vacuo to an oil that is triturated with two 20-ml volumes of $Et_2O$. The crude acyl product is purified by reversed-phase HPLC and analyzed as described in Method A.

The specific compounds in the examples summarized in Tables I through X which follow are compounds of formula 1:

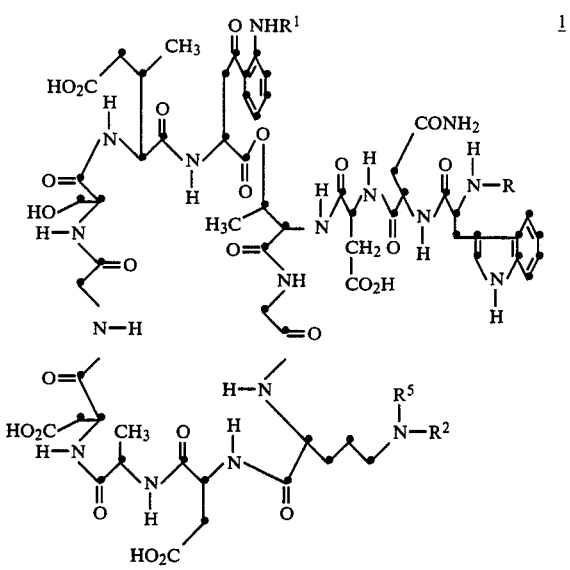

TABLE I

Preparation of $N_{Trp}$—Monoacyl Derivatives of A-21978C Cyclic Peptides

| Example No. | Compound[a] R | Method of Prep. | Nucleus wt (mg) | Acyl. Agent wt (mg) | Reaction Time (hr) | Intermediate[b] HPLC Eluent[c] | Product HPLC Eluent[c] | wt (mg) |
|---|---|---|---|---|---|---|---|---|
| 1 | $CH_3(CH_2)_5CO-$ | B | 1028 | 800 | 20 | 55:15:30 | 50:15:35 | 205 |
| 2 | $CH_3(CH_2)_6CO-$ | A | 1950 | 3421 | 3 | 50:15:35 | 55:15:30 | 355 |
| 3 | $CH_3(CH_2)_6CO-$ | B | 1000 | 350 | 24 | 50:15:35 | 115:15:64 | 264 |
| 4 | $CH_3(CH_2)_7CO-$ | A | 2000 | 882 | 2 | not purified | 50:15:35 | 212 |
| 5 | $CH_3(CH_2)_7CO-$ | B | 1000 | 400 | 20 | not purified | 50:15:35 | 240 |
| 6 | $CH_3(CH_2)_8CO-$ | A | 2160 | 4595 | 5 |  | 45:15:40 | 334 |
| 7 | $CH_3(CH_2)_9CO-$ | B | 1000 | 288 | 22 | not purified | 45:15:40 | 392 |
| 8 | $CH_3(CH_2)_{10}CO-$ | A | 1000 | 3406 | 2 |  | 45:15:40 | 370 |
| 9 | $CH_3(CH_2)_{11}CO-$ | B | 1000 | 800 | 24 | 10:15:75 | 40:15:45 | 313 |
| 10 | $CH_3(CH_2)_{12}CO-$ | B | 1000 | 812 | $22^d$ | 50:15:35 | $1:0:1^e$ | 267 |
| 11 | $CH_3(CH_2)_{12}CO-$ | B | 1000 | 900 | 20 | 50:15:35 | 50:15:35 | 215 |
| 12 | $CH_3(CH_2)_{13}CO-$ | B | 1000 | 1031 | $22^d$ | not purified | $35:10:55^e$ | 337.8 |
| 13 | $CH_3(CH_2)_{14}CO-$ | B | 1000 | 744 | $18^d$ | not purified | $2:0:3^e$ | 257 |
| 14 | $CH_2=CH-(CH_2)_8CO-$ | B | 1000 | 237 | 20 | 20:15:65 | 45:15:40 | 290 |
| 15 | $CH_3(CH_2)_3CH=CH(CH_2)_7CO-$ | B | 1000 | 400 | 48 | not purified | 40:15:45 | 215 |
| 16 | $CH_3CH_2CH=CHCH_2CH=CH-CH_2CH=CH(CH_2)_7CO-$ | B | 1000 | 400 | 28 | 35:15:50 | 35:15:50 | 283 |

[a] $R^1$, $R^2$ = H,
[b] $N_{Trp}$Acyl—$N_{Orn}$—tBOC,
[c] $H_2O:CH_3OH:CH_3CN$ (v:v:v) containing 0.2% pyridine and 0.2% HOAc
[d] Reaction temperature maintained at 5° C.,
[e] Containing 1% pyridine and 1% HOAc

TABLE II
Characteristics of N$_{Trp}$—Monoacyl Derivatives of A-21978C Cyclic Peptides

| Compound No. | R | R$^1$ | R$^2$ | R$_f{}^a$ | Anal. HPLC Eluent$^b$ | UV $\epsilon_{\lambda max}$220 nm | UV $\epsilon_{\lambda max}$260 nm |
|---|---|---|---|---|---|---|---|
| 1 | CH$_3$(CH$_2$)$_5$CO— | H | H | 0.85 | 60:15:25 | 48,100 | 11,400 |
| 2 | CH$_3$(CH$_2$)$_6$CO— | H | H | 0.80 | 60:15:25 | 46,900 | 10,500 |
| 3 | CH$_3$(CH$_2$)$_7$CO— | H | H | 0.75 | 45:15:40 | 46,000 | 11,000 |
| 4 | CH$_3$(CH$_2$)$_8$CO— | H | H | 0.70 | 45:15:40 | 46,500 | 10,000 |
| 5 | CH$_3$(CH$_2$)$_9$CO— | H | H | 0.65 | 45:15:40 | 46,200 | 10,400 |
| 6 | CH$_3$(CH$_2$)$_{10}$CO— | H | H | 0.59 | 45:15:40 | 44,000 | 9,500 |
| 7 | CH$_3$(CH$_2$)$_{11}$CO— | H | H | 0.53 | 45:15:40 | 48,500 | 9,800 |
| 8 | CH$_3$(CH$_2$)$_{12}$CO— | H | H | 0.42 | 50:0:49$^c$ | 48,447 | 9,170 |
| 9 | CH$_3$(CH$_2$)$_{13}$CO— | H | H | 0.34 | 1:0:1$^c$ | 50,172 | 9,751 |
| 10 | CH$_3$(CH$_2$)$_{14}$CO— | H | H | 0.25 | 39:0:60$^c$ | 54,000 | 12,000 |
| 11 | CH$_2$=CH—(CH$_2$)$_8$CO— | H | H | 0.70 | 45:15:40 | 44,000 | 9,200 |
| 12 | CH$_3$(CH$_2$)$_3$CH=CH(CH$_2$)$_7$CO— | H | H | 0.54 | 45:15:40 | 45,000 | 9,600 |
| 13 | CH$_3$CH$_2$CH=CHCH$_2$CH=CH—CH$_2$CH=CH(CH$_2$)$_7$CO— | H | H | 0.50 | 45:15:40$^c$ | 50,000 | 11,600 |

$^a$R$_f$ by reversed-phase silica-gel TLC (Whatman KC$_{18}$ with fluorescent indicator) and H$_2$O:CH$_3$OH:CH$_3$CN (45:15:40) with 0.2% pyridine and 0.2% HOAc solvent system
$^b$H$_2$O:CH$_3$OH:CH$_3$N (v:v:v) containing 0.2% pyridine and 0.2% HOAc
$^c$Containing 1% pyridine and 1% HOAc

TABLE III
Preparation of N$_{Trp}$—N$_{Orn}$—Diacyl A-21978C Derivatives

| Example No. | R | R$^1$ | R$^2$ | Method of Prep. | Starting Material wt (mg) | Acyl. Agent wt (mg) | Reaction Time (hr) | HPLC Eluent$^a$ | Product Wt (mg) |
|---|---|---|---|---|---|---|---|---|---|
| 17 | CH$_3$CH$_2$CH(CH$_3$)(CH$_2$)$_6$CO— | H | CH$_3$CO— | A | 409 | 2208 | 1.5 | 45:15:40 | 273 |
| 18 | CH$_3$CH$_2$CH(CH$_3$)(CH$_2$)$_6$CO— | H | CH$_3$CO— | B | 946 | 139 | 17 | 95:30:75 | 365 |
| 19 | CH$_3$CH$_2$CH(CH$_3$)(CH$_2$)$_6$CO— | H | HOCOCH$_2$CH$_2$CO— | C$^b$ | 500 | 62 | 20 | 45:15:40 | 201 |
| 20 | CH$_3$(CH$_2$)$_6$CO— | H | CH$_3$(CH$_2$)$_6$CO— | B | 500 | 530 | 18$^c$ | 35:25:40 | 60 |
| 21 | CH$_3$(CH$_2$)$_9$CO— | H | CH$_3$(CH$_2$)$_9$CO— | B | 1000 | 292 | 24 | 45:15:40 | 158 |
| 22 | CH$_3$(CH$_2$)$_9$CO— | H | CH$_3$(CH$_2$)$_9$CO— | B | 1000 | 1119 | 18$^c$ | 2:0:3$^d$ | 366 |
| 23 | CH$_3$(CH$_2$)$_{11}$CO— | H | CH$_3$(CH$_2$)$_{11}$CO— | B | 1000 | 1066.9 | 18$^c$ | 2:0:3$^d$ | 245.9 |
| 24 | CH$_3$CH$_2$CH(CH$_3$)(CH$_2$)$_6$CO | H | t-BOC | D$^e$ | | | | | |
| 25 | Cbz | H | CH$_3$(CH$_2$)$_{10}$CO— | | 1000 | 123 | 20 | | 550 |

$^a$H$_2$O:CH$_3$OH:CH$_3$N (v:v:v) containing 0.2% pyridine and 0.2% HOAc
$^b$Succinic anhydride, 90% pyridine
$^c$Reaction temperature maintained at 5° C.
$^d$Containing 1% pyridine and 1% HOAc
$^e$(t-BOC)$_2$/H$_2$O

TABLE IV
Characteristics of N$_{Trp}$, N$_{Orn}$—Diacyl A-21978C Derivatives

| Compound No. | R | R$^1$ | R$^2$ | R$_f{}^a$ | Anal. HPLC Eluent$^b$ | UV $\epsilon_{\lambda max}$220 nm | UV $\epsilon_{\lambda max}$260 nm |
|---|---|---|---|---|---|---|---|
| 14 | CH$_3$CH$_2$CH(CH$_3$)(CH$_2$)$_6$CO— | H | CH$_3$CO— | 0.69 | 45:15:40 | 46,000 | 10,400 |
| 15 | CH$_3$CH$_2$CH(CH$_3$)(CH$_2$)$_6$CO— | H | HOCO(CH$_2$)$_2$CO— | 0.75 | 45:15:40 | 47,000 | 11,000 |
| 16 | CH$_3$(CH$_2$)$_6$CO— | H | CH$_3$(CH$_2$)$_6$CO— | 0.67 | 45:15:40$^c$ | 45,000 | 9,000 |
| 17 | CH$_3$(CH$_2$)$_9$CO— | H | CH$_3$(CH$_2$)$_9$CO— | 0.31 | 30:15:55 45:15:40$^c$ | 48,200 | 8,000 |
| 18 | CH$_3$(CH$_2$)$_{11}$CO— | H | CH$_3$(CH$_2$)$_{11}$CO— | 0.03 | 45:15:40$^c$ | 49,000 | 9,000 |
| 19 | CH$_3$CH$_2$CH(CH$_3$)(CH$_2$)$_6$CO— | H | t-BOC | NT$^d$ | NT | NT | NT |
| 20 | Cbz | H | CH$_3$(CH$_2$)$_{10}$CO— | 0.58 | NT | NT | NT |

$^a$R$_f$ by reversed-phase silica-gel TLC (Whatman KC$_{18}$ with fluorescent indicator; solvent system H$_2$O:CH$_3$OH:CH$_3$CN (45:15:40) with 0.2% pyridine and 0.2% HOAc
$^b$H$_2$O:CH$_3$OH:CH$_3$CN (v:v:v) containing 0.2% pyridine and 0.2% HOAc
$^c$Containing 1% pyridine and 1% HOAc
$^d$NT = not tested

TABLE V
Preparation of N$_{Trp}$, N$_{Kyn}$—Diacyl Derivative$^a$

| Example No. | R, R$^1$ | R$^2$ | Method of Prep. | Starting Material wt (g) | Acyl Agent wt (g) | Reaction Time (hr) | tBOC Diacyl Intermediate HPLC Eluent$^a$ | Product HPLC Eluent$^b$ | wt (mg) |
|---|---|---|---|---|---|---|---|---|---|
| 26 | CH$_3$(CH$_2$)$_8$CO— | H | B | 15 | 15 | 30 | 50:15:35 | 50:15:35 | 211 |

$^a$See Example 28, infra
$^b$H$_2$O:CH$_3$OH:CH$_3$CN (v:v:v) containing 0.2% pyridine and 0.2% HOAc

TABLE VI

Characteristics of $N_{Trp}$, $N_{Kyn}$—Diacyl Derivative

| Compound No. | R | $R^1$ | $R^2$ | $R_f{}^a$ | Anal. HPLC Eluent[b] | UV $\epsilon_{\lambda max}$220 nm | $\epsilon_{\lambda max}$260 nm |
|---|---|---|---|---|---|---|---|
| 21 | $CH_3(CH_2)_8CO-$ | $CH_3(CH_2)_8CO-$ | H | 0.66 | 61:15:23:1 | 41.800 | 11,500 |

[a] $R_f$ by reversed-phase silica-gel TLC (Whatman $KC_{18}$ with fluorescent indicator) and $H_2O:CH_3OH:CH_3CN$ (45:15:40) with 0.2% pyridine and 0.2% HOAc solvent system
[b] $H_2O:CH_3OH:CH_3CN:NH_4OAc$ containing 0.2% pyridine and 0.2% HOAc

EXAMPLE 27

$N_{Trp}$-(n-Decanoyl) A-21978C Nucleus (Compound 4)

The following procedure illustrates the large-scale preparation of compounds by the active-ester method.

A. Preparation of 2,4,5-Trichlorophenyl n-decanoate

A solution of decanoyl chloride (Pfaltz and Bauer, 5.6 ml) and 2,4,5-trichlorophenol (5.6 g) in diethyl ether (1 L) and pyridine (120 ml) is stirred for 4 hours. The reaction mixture is filtered and dried in vacuo. The 2,4,5-trichlorophenyl n-decanoate is purified on a silica-gel column (Woelm), using toluene as the eluent. Fractions are monitored by TLC, using short-wave UV for detection. Appropriate fractions are pooled and dried in vacuo to give 10.4 g of 2,4,5-trichlorophenyl n-decanoate.

B. Acylation of $N_{Orn}$-t-BOC-A-21978C Nucleus with 2,4,5-Trichlorophenyl n-decanoate A solution of $N_{Orn}$-t-BOC A-21978C nucleus (15.0 g) and 2,4,5-trichlorophenyl n-decanoate (15.0 g) in dry DMF (500 ml) is stirred under $N_2$ at ambient temperature for 25 hours. The mixture is then stirred at 60° C. for 5 hours or until TLC shows reaction completion. The reaction mixture is concentrated in vacuo to about 200 ml and is stirred with 1.2 liters of $Et_2O$/toluene (5:1). The product is separated by filtration, washed with $Et_2O$, and dried under vacuum to give 15.05 g of the $N_{Trp}$-(n-decanoyl)-$N_{Orn}$-t-BOC A-21978C nucleus intermediate (formula 1; R=n-decanoyl, $R^1$=H, $R^2$=t-BOC).

C. Purification of $N_{Trp}$-(n-Decanoyl)-$N_{Orn}$-t-BOC-A-21978C Nucleus

The $N_{Trp}$-(n-decanoyl)-$N_{Orn}$-t-BOC-A-21978C nucleus intermediate is purified in the following manner: The crude preparation is dissolved in about 50 ml of the eluting solvent system, and this is purified by HPLC, using the Waters Prep/500 system containing a cartridge packed with reversed-phase $C_{18}$ silica-gel adsorbent. The system is eluted with $H_2O:MeOH:CH_3CN$ (50:15:35) containing 0.2% pyridine and 0.2% HOAc. Fractions are monitored by UV at 280 nm. Appropriate fractions are combined and dried in vacuo to give 8.56 g of purified $N_{Trp}$-(n-decanoyl)-$N_{Orn}$-t-BOC-A-21978C nucleus.

D. Removal of the $N_{Orn}$-t-BOC Group

The t-BOC group is removed by stirring $N_{Trp}$-(n-decanoyl)-$N_{Orn}$-t-BOC A-21978C nucleus (1.47 g) in 15 ml of trifluoroacetic acid/1,2-ethanedithiol (10:1) at ambient temperature for 3 minutes. The reaction mixture is dried in vacuo, and the residue is triturated with $Et_2O$ (50 ml). After a 20-ml $Et_2O$ wash, the triturate is dried in vacuo to give 2.59 g of crude $N_{Trp}$-(n-decanoyl)-A-21978C nucleus (formula 1: R=n-decanoyl; $R^1$ and $R^2$=H).

E. Purification of $N_{Trp}$-(n-Decanoyl)-A-21978C Nucleus

The crude $N_{Trp}$-(n-decanoyl)-A-21978C nucleus is purified by reversed-phase HPLC in the following manner: The sample (2.59 g), dissolved in 4.0 ml of $H_2O$:-MeOH:$CH_3CN$:pyridine:HOAc (50:15:35:2:2), is injected into a 33-×1-inch stainless-steel column packed with LP-1/$C_{18}$ adsorbent. The column is eluted with this same solvent system. Elution is performed at a pressure of 1200-1700 psi with a flow rate of 10-12 ml/min, using an LDC duplex pump (Milton-Roy). The effluent is monitored by a UV detector (Isco Model UA-5, Instrument Specialist Co., 4700 Superior Avenue, Lincoln, NB 68504) at 280 nm. Fractions (20-24 ml) are collected every two minutes. The desired fractions, as indicated by antimicrobial activity, are combined and dried in vacuo to give 1.05 g of product.

This purification procedure was repeated with 4.35 g, 4.25 g, 2.14 g, 2.00 g and 1.75 g crude starting derivative to give a total of 5.58 g of purified $N_{Trp}$-(n-decanoyl)-A-21978C nucleus.

EXAMPLE 28

$N_{Trp}$-(n-Decanoyl)-$N_{Kyn}$-(n-decanoyl)-A-21978C (Compound 21)

$N_{Trp}$-(n-Decanoyl)-$N_{Kyn}$-(n-decanoyl)-A-21978C nucleus (formula 1: R and $R^1$=n-decanoyl; $R^2$=H) is a minor reaction product in the preparation of the $N_{Trp}$-(n-decanoyl) derivative of Example 27. It is isolated during the reversed-phase HPLC purification described in Section E. Desired fractions are combined and dried in vacuo to give 211 mg of crude product. The compound is purified by analytical HPLC ($C_{18}$ Microbondapak, Waters Co.), using $H_2O$:MeOH:$CH_3CN$:$N$-$H_4OH$:HOAc (6:23:15:0.5) as the eluent system (32 repetitions, 500 μg each injected sample) to give 4.4 mg of $N_{Trp}$-(n-decanoyl)-$N_{Kyn}$-(n-decanoyl)-A-21978C nucleus, identified by 360 MHz proton NMR.

EXAMPLE 29

$N_{Trp}$-Cbz-$N_{Orn}$-Lauroyl A-21978C Nucleus (Compound 20)

This method involves protecting the tryptophan α-$NH_2$ of $N_{Orn}$-t-BOC-A-21978C nucleus with a Cbz group, then removing the t-BOC group and acylating (at the ornithine α-$NH_2$) with the trichlorophenyl-lauroyl ester.

A. Preparation of $N_{Trp}$-Cbz-$N_{Orn}$-t-BOC-A-21978C Nucleus $N_{Orn}$-t-BOC-A-21978C nucleus (1.0 g) is dissolved in DMF (150 ml) and warmed to 60° C. N,O-bis-trimethylsilylacetamide (0.55 ml) is added, and then benzyl pentachlorophenyl carbonate (257 mg) is added. After being stirred for 20 hours, the reaction mixture is concentrated to a volume of about 20-25 ml. Water (100 ml) is added, and the pH of this solution is adjusted to 6.0 with 1N NaOH. The mixture is washed with Et₂O (6 times, 200-ml volumes) and then is lyophilized.

The crude derivative is purified by reversed-phase HPLC as follows: The sample, dissolved in about 6 ml of H₂O:MeOH:CH₃CN:pyridine:HOAc (55:15:30:2:2), is injected into a 33-×½-inch stainless-steel column packed with LP-1/C₁₈ support. The desired fractions are located by UV absorption (280 nm) and antimicrobial activity. These fractions are then combined and lyophilized to give 951 mg of the N$_{Trp}$-Cbz-N$_{Orn}$-t-BOC A-21978C nucleus derivative.

B. Removal of t-BOC Group

The t-BOC group is removed by dissolving the intermediate at 50 mg/ml in trifluoroacetic acid:anisole:triethylsilane (10:1:1) at −10° C. for 3 minutes. The reaction is concentrated to an oil that is triturated with two 25-ml volumes of Et₂O to give 520 mg of crude N$_{Trp}$-Cbz-A-21978C nucleus.

C. Acylation of N$_{Trp}$-Cbz-A-21978C Nucleus

The N$_{Trp}$-Cbz-A-21978C nucleus is acylated by the trichlorophenyl active-ester acylation method. N$_{Trp}$-Cbz-A-21978C (520 mg) is added to a solution of 1-hydroxybenzotriazole (7 mg) and lauroyltrichlorophenol active ester (123 mg) in pyridine (150 ml). After being stirred for 20 hours at 60° C., the reaction mixture is concentrated to a residue that is triturated with Et₂O (3 times, 25-ml volumes) to give N$_{Trp}$-Cbz-N$_{Orn}$-lauroyl-A-21978C nucleus (550 mg).

EXAMPLE 30

Preparation of Schiff's Bases and Reduced Schiff's Bases

Several reactions were carried out as follows: A-21978C nucleus (40 mg) was dissolved in water (2 ml). The pH of the solution was adjusted from 4 to 9 with 1N NaOH. Aliquots (0.5 ml) of this solution were then mixed with each of the following aldehydes (5 μl):
(1) heptaldehyde
(2) octyl aldehyde
(3) decyl aldehyde
(4) undecyl aldehyde
in methanol (4 ml). The reactions were stirred overnight at room temperature. The Schiff's bases which formed were reduced with NaBH₃CN (2.5 mg per reaction) for 5 minutes at room temperature.

The reactions were examined by silica-gel TLC, using a CH₃CN:H₂O (7:3) solvent system, and by assay against *Staphylococcus aureus*. The Schiff's bases were not active against *S. aureus* in this test, perhaps due to their instability under the assay conditions. In each reduced reaction two factors were produced. These compounds were active against *S. aureus* and had a similar mobility in the TLC system, giving evidence that the following compounds of the formula 1 were produced (in each case R¹ and R³ are hydrogen):

Preparation of Schiff's Bases and Reduced Schiff's Bases

| Reaction of A21978C with | R, R⁴ Group | R², R⁵ Group | Active vs S. aureus[a] |
|---|---|---|---|
| heptaldehyde | CH₃(CH₂)₅CH= | H | no |
|  | CH₃(CH₂)₆— | H | yes |
|  | CH₃(CH₂)₅CH= | CH₃(CH₂)₅CH= | no |
|  | CH₃(CH₂)₆— | CH₃(CH₂)₆— | yes |
| octyl aldehyde | CH₃(CH₂)₆CH= | H | no |
|  | CH₃(CH₂)₇— | H | yes |
|  | CH₃(CH₂)₆CH= | CH₃(CH₂)₆CH= | no |
|  | CH₃(CH₂)₇— | CH₃(CH₂)₇— | yes |
| decyl aldehyde | CH₃(CH₂)₈CH= | H | no |
|  | CH₃(CH₂)₉— | H | yes |
|  | CH₃(CH₂)₈CH= | CH₃(CH₂)₈C= | no |
|  | CH₃(CH₂)₉— | CH₃(CH₂)₉— | yes |
| undecyl aldehyde | CH₃(CH₂)₉CH= | H | no |
|  | CH₃(CH₂)₁₀— | H | yes |
|  | CH₃(CH₂)₉CH= | CH₃(CH₂)₉CH= | no |
|  | CH₃(CH₂)₁₀— | CH₃(CH₂)₁₀— | yes |

[a]The lack of activity of the Schiff's bases in this test may reflect their instability under the test conditions.

EXAMPLE 31

Preparation of N$_{Trp}$-Lauraldehyde Schiff's Base and N$_{Trp}$, N$_{Orn}$-Di-Lauraldehyde Schiff's Base and Their Reduced Schiff's Bases (Compounds 22 and 23)

A-21978C nucleus (1 g) was dissolved in water (50 ml); a solution of dodecyl aldehyde (500 μl) in methanol (200 ml) was added. The reaction mixture was stirred overnight at room temperature. The reaction was then reduced for 50 minutes by the addition of NaBH₃CN (291 mg). The reaction mixture was filtered under vacuum, using Whatman No. 1 paper to remove particulates. The supernatant was concentrated to an aqueous solution which was lyophilized to give 1.256 g of product. This product was evaluated by analytical HPLC and purified by preparative reverse-phase HPLC in portions. Each portion (350 mg) was dissolved in 50% aqueous methanol (6 ml), sonicating and heating to dissolve the material. The solution was then passed over a 1.5-×80-cm LP₁-C₁₈ column, eluting with CH₃OH:CH₃CN:H₂O (25:40:35) containing 0.2% pyridine and 0.2% acetic acid at a flow rate of about 7.5 ml/min. Elution was monitored by UV at 280 nm. Fractions containing the desired products were combined to give a total of 104 mg of N$_{Trp}$-(n-dodecyl)-A-21978C nucleus (Compound 22) and 19.2 mg of N$_{Trp}$-(n-dodecyl)-N$_{Orn}$-(n-dodecyl)-A-21978C nucleus (Compound 23).

EXAMPLE 32

The antibacterial activity of the compounds of formula 1 can be demonstrated in vitro. The results of the antibacterial testing of representative compounds of formula 1 wherein R³, R⁴ and R⁵ are all hydrogen, using standard agar-plate disc-diffusion tests, are set forth in Table VII. In Table VII activity is measured by the size (diameter in mm) of the observed zone in which growth of the microorganism is inhibited by the test compound.

TABLE VII

Antibacterial Activity of Formula 1 Compounds by the Agar-Plate Disc-Diffusion Test

| Compound No. | R | $R^1$ | $R^2$ | Staphylococcus aureus ATCC 6738P | Bacillus subtilis ATCC 6633 | Micrococcus luteus ATCC 9341 | B. subtilis ATCC 6633[b] |
|---|---|---|---|---|---|---|---|
| 1 | $CH_3(CH_2)_5CO-$ | H | H | 17 | 15 | 21 | 16 |
| 2 | $CH_3(CH_2)_6CO-$ | H | H | 23 | 18 | 23 | 20 |
| 3 | $CH_3(CH_2)_7CO-$ | H | H | 20 | 16 | 18 | 27 |
| 4 | $CH_3(CH_2)_8CO-$ | H | H | 24 | 20 | 22 | 29 |
| 5 | $CH_3(CH_2)_9CO-$ | H | H | 19 | 19 | 21 | 21 |
| 6 | $CH_3(CH_2)_{10}CO-$ | H | H | 25 | 20 | 19 | 32 |
| 7 | $CH_3(CH_2)_{11}CO-$ | H | H | 21 | 17 | 19 | 29 |
| 8 | $CH_3(CH_2)_{12}CO-$ | H | H | 22 | 21 | 21 | 28 |
| 9 | $CH_3(CH_2)_{13}CO-$ | H | H | 20 | 19 | 19 | 24 |
| 10 | $CH_3(CH_2)_{14}CO-$ | H | H | 19 | 17 | 17 | 23 |
| 11 | $CH_2=CH-(CH_2)_8CO-$ | H | H | 21 | 17 | 20 | 25 |
| 12 | $CH_3(CH_2)_3CH=CH(CH_2)_7CO-$ | H | H | 22 | 19 | 20 | 30 |
| 13 | $CH_3CH_2CH=CHCH_2CH=CH-CH_2CH=CH(CH_2)_7CO-$ | H | H | 15 | 13 | 20 | 14 |
| 14 | $CH_3CH_2CH(CH_3)(CH_2)_6CO-$ | H | $CH_3CO-$ | 21 | 18 | 20 | 25 |
| 15 | $CH_3CH_2CH(CH_3)(CH_2)_6CO-$ | H | $HOCO(CH_2)_2CO-$ | 21 | 18 | 19 | 25 |
| 16 | $CH_3(CH_2)_6CO-$ | H | $CH_3(CH_2)_6CO-$ | 11 | tr[c] | 10 | 17 |
| 17 | $CH_3(CH_2)_9CO-$ | H | $CH_3(CH_2)_9CO-$ | 17 | 13 | 14 | 20 |
| 18 | $CH_3(CH_2)_{11}CO-$ | H | $CH_3(CH_2)_{11}CO-$ | 12 | tr | — | 13 |
| 19 | $CH_3CH_2CH(CH_3)(CH_2)_6CO-$ | H | t-BOC | 14 | 11 | 10 | 22 |
| 20 | Cbz | H | $CH_3(CH_2)_{10}CO-$ | 15 | 10 | 17 | 23 |

[a]Compounds were suspended in water at a concentration of 1 mg/ml; a 7 mm disc was dipped into the suspension and then placed on the agar surface; incubation: 24–48 hours at 25–37° C.
[b]Grown on minimal nutrient agar
[c]tr = trace In the agar-plate disc-diffusion tests summarized in Table VII compounds 1–20 did not show activity against the following organisms at the levels tested: *Saccharomyces cerevisiae* ATCC 2366, *Neurospora crassa*, *Candida albicans*, *Trichophyton mentagrophytes*, *Proteus vulgaris* ATCC 9484, *Salmonella gallinarum*, *Escherichia coli* ATCC 4157, *Pseudomonas aeruginosa* ATCC 9027, *Serratia marcescens* NRRL B284, or *Pseudomonas solanacearum*.

The results of antibacterial testing of representative compounds of formula 1 by standard agar-dilution tests are summarized in Table VIII. In Table VIII activity is measured by the minimal inhibitory concentration (MIC), i.e. the lowest concentration of compound at which growth of the microorganism is inhibited by the test compound.

TABLE VIII

Antibiotic Activity of A-21978C Cyclic Peptides

| Test Organism | MIC Values of Test Compounds[a] | | | | | | | | | | |
|---|---|---|---|---|---|---|---|---|---|---|---|
| | 1 | 2[d] | 3 | 4[e] | 5[d] | 6[e] | 7 | 8 | 9 | 10 | 11 |
| *Staphylococcus aureus* X1.1 | 8 | 4 | 2 | 1,0.5 | 0.25 | 0.5,0.5 | 0.125 | 0.5,1 | 1 | 1 | 0.5 |
| *Staphylococcus aureus* V41[b] | 8 | 4 | 2 | 1,0.5 | 0.25 | 0.5,1 | 0.125 | 0.5,2 | 1 | 1 | 0.5 |
| *Staphylococcus aureus* X400[c] | 8 | 8 | 4 | 2,1 | 0.5 | 1,1 | 0.5 | 1,2 | 2 | 2 | 0.5 |
| *Staphylococcus aureus* S13E | 8 | 4 | 2 | 1,0.5 | 0.5 | 0.5,0.5 | 0.25 | 1,2 | 1 | 1 | 0.25 |
| *Staphylococcus epidermidis* EPI1 | 16 | 8 | 4 | 2,1 | 0.5 | 1,1 | 0.5 | 1,4 | 2 | 2 | 1 |
| *Staphylococcus epidermidis* EPI2 | 8 | 4 | 2 | 1,0.5 | 0.5 | 1,1 | 0.5 | 2,2 | 4 | 2 | 1 |
| *Streptococcus pyogenes* C203 | 2 | 1 | 0.25 | 0.25, 0.125 | 0.125 | 0.125, 0.25 | 0.25 | 0.5,2 | 1 | 1 | 0.5 |
| *Streptococcus pneumoniae* Park I | 8 | 8 | 2 | 1,0.5 | 0.25 | 0.25, 0.25 | 0.25 | 0.03, 0.125 | 0.06 | 0.06 | 0.25 |
| *Streptococcus pneumoniae* Group D X66 | 128 | 64 | 32 | 16,16 | 2 | 2,4 | 0.03 | 0.5,2 | 2 | 2 | 1 |
| *Streptococcus pneumoniae* Group 9960 | 128 | 16 | 8 | 2,2 | 0.5 | 0.5,0.5 | 32 | 0.125, >128 | 0.25 | 0.25 | 0.5 |

| Test Organism | 12 | 13 | 14[e] | 15[e] | 16 | 17[d] | 18 | 20 | 21 | 22[d] | 23 |
|---|---|---|---|---|---|---|---|---|---|---|---|
| *Staphylococcus aureus* X1.1 | 1 | >128 | 4,4 | 4,4 | 8 | 1 | 8 | 8 | 1 | 0.5 | 8 |
| *Staphylococcus aureus* V41[b] | 1 | >128 | 4,4 | 8,8 | 16 | 4 | 64 | 16 | 4 | 1 | 8 |
| *Staphylococcus aureus* X400[c] | 2 | >128 | 8,8 | 4,8 | 8 | 4 | >128 | 32 | 32 | 1 | 16 |
| *Staphylococcus aureus* S13E | 1 | >128 | 8,4 | 4,8 | 8 | 1 | >128 | 8 | 16 | 0.5 | 8 |
| *Staphylococcus epidermidis* EPI1 | 2 | >128 | 8,8 | 8,8 | 16 | 8 | >128 | 32 | 2 | 1 | 8 |
| *Staphylococcus epidermidis* EPI2 | 2 | >128 | 8,4 | 8,8 | 16 | 8 | >128 | 32 | 2 | 1 | 8 |
| *Streptococcus pyogenes* C203 | 0.5 | >128 | 1,1 | 1,1 | 4 | 0.25 | 1 | 4 | 0.125 | 0.5 | 4 |
| *Streptococcus pneumoniae* Park I | 0.5 | >128 | 2,2 | 2,4 | 4 | 0.125 | 0.5 | — | 0.5 | 1 | 8 |
| *Streptococcus pneumoniae* Group D X66 | 2 | >128 | 64,32 | 64,64 | >128 | 8 | >128 | 128 | >128 | 4 | 32 |
| *Streptococcus pneumoniae* | 1 | >128 | 32,8 | 32,32 | 64 | 8 | >128 | 64 | 128 | 1 | 8 |

TABLE VIII-continued

Antibiotic Activity of A-21978C Cyclic Peptides

| Test Organism | MIC Values of Test Compounds[a] |
|---|---|
| Groups 9960 | |

[a]MIC in mcg/ml; compound numbers from Tables II, IV and VI and Example 31
[b]Penicillin-resistant strain
[c]Methicillin-resistant-strain
[d]Median value from three tests
[e]Two experiments In the agar-dilution tests summarized in Table VIII compounds 1–23 were not active against strains of the following organisms at the levels tested: *Haemophilus influenzae, Shigella sonnei, Escherichia coli, Klebsiella pneumoniae, Enterobacter aerogenes, Enterobacter cloacae, Salmonella typhi, Pseudomonas aeruginosa, Serratia marcescens, Proteus morganii, Proteus inconstans, Proteus rettgeri, Citrobacter freundii* and *Bordetella bronchiseptica.*

The A-21978C cyclic peptides of formula 1 have shown in vivo antimicrobial activity against experimental bacterial infections. When two doses of test compound were administered subcutaneously or orally to mice in illustrative infections, the activity observed was measured as an $ED_{50}$ value [effective dose in mg/kg to protect fifty percent of the test animals: See Warren Wick, et al., *J. Bacteriol.* 81, 233–235 (1961)]. The $ED_{50}$ values observed for representative A-21978C compounds of formula 1 wherein $R^3$, $R^4$ and $R^5$ are all hydrogen are given in Table IX.

TABLE IX

In Vivo Activity of A-21978C Cyclic Peptides

| | | | | $ED_{50}$ Values[a] | | |
|---|---|---|---|---|---|---|
| | | | | *Staphylococcus aureus* | *Streptococcus pyogenes* | |
| Compound No. | Formula 1 Compound R | $R^1$ | $R^2$ | Subcutaneous | Subcutaneous | Oral |
| 1 | $CH_3(CH_2)_5CO-$ | H | H | 2.65 | 1.49,5.1[b] | NT[c] |
| 2 | $CH_3(CH_2)_6CO-$ | H | H | 3.75,1.4 | <2.2,0.65,1.9[d] | >200 |
| 3 | $CH_3(CH_2)_7CO-$ | H | H | 0.5 | 0.14,0.243 | 92,117 |
| 4 | $CH_3(CH_2)_8CO-$ | H | H | 0.28 | 0.03 | 66 |
| 5 | $CH_3(CH_2)_9CO-$ | H | H | 0.37 | 0.13 | 138 |
| 6 | $CH_3(CH_2)_{10}CO-$ | H | H | 0.44 | 0.05 | 69 |
| 7 | $CH_3(CH_2)_{11}CO-$ | H | H | 0.54 | 0.046 | 45 |
| 8 | $CH_3(CH_2)_{12}CO-$ | H | H | 1.17,3.08 | 0.98, 0.20, <0.54 | <50,<200 |
| 9 | $CH_3(CH_2)_{13}CO-$ | H | H | 8.3 | <0.5,0.18 | >200 |
| 10 | $CH_3(CH_2)_{14}CO-$ | H | H | >1.1 | 0.18 | >200 |
| 11 | $CH_2=CH-(CH_2)_8CO-$ | H | H | 0.93 | 0.068 | 138 |
| 12 | $CH_3(CH_2)_3CH=CH(CH_2)_7CO-$ | H | H | 3.28 | 0.134 | 75 |
| 14 | $CH_3CH_2CH(CH_3)(CH_2)_6CO-$ | H | $CH_3CO-$ | 1.3 | 2.2,1.9 | 163,>200 |
| 15 | $CH_3CH_2CH(CH_3)(CH_2)_6CO-$ | H | $HOCO-(CH_2)_2CO-$ | 6.27 | 1.4 | >200 |
| 17 | $CH_3(CH_2)_9CO-$ | H | $CH_3(CH_2)_9-CO-$ | >35 | 2.85 | >200 |
| 22 | $CH_3(CH_2)_{11}-$ | H | H | 1.25 | 1.1,0.85 | >200 |

[a]mg/kg × 2,
[b]Two Experiments,
[c]Not Tested,
[d]Three Experiments

The results of toxicity tests on some A-21978C cyclic peptides of formula 1 wherein $R^3$, $R^4$ and $R^5$ are all hydrogen are summarized in Table X.

TABLE X

Toxicity of A-21978C Cyclic Peptides

| Compound No. | Formula 1 Compound R | $R^1$ | $R^2$ | $LD_{50}$ (mg/kg) in Mice[a] |
|---|---|---|---|---|
| 1 | $CH_3(CH_2)_5CO-$ | H | H | >600 |
| 2 | $CH_3(CH_2)_6CO-$ | H | H | >600 |
| 3 | $CH_3(CH_2)_7CO-$ | H | H | >600 |
| 4 | $CH_3(CH_2)_8CO-$ | H | H | >300 |
| 5 | $CH_3(CH_2)_9CO-$ | H | H | >600 |
| 6 | $CH_3(CH_2)_{10}CO-$ | H | H | 144,265[b] |
| 7 | $CH_3(CH_2)_{11}CO-$ | H | H | 112.5 |
| 8 | $CH_3(CH_2)_{12}CO-$ | H | H | 62.5,<150 |
| 9 | $CH_3(CH_2)_{13}CO-$ | H | H | 56.25 |
| 10 | $CH_3(CH_2)_{14}CO-$ | H | H | 50 |
| 11 | $CH_2=CH-(CH_2)_8CO-$ | H | H | ≧500 |
| 12 | $CH_3(CH_2)_3CH=CH(CH_2)_7CO-$ | H | H | 450 |
| 14 | $CH_3CH_2CH(CH_3)(CH_2)_6CO-$ | H | $CH_3CO-$ | >600,600 |
| 15 | $CH_3CH_2CH(CH_3)(CH_2)_6CO-$ | H | $HOCO(CH_2)_2CO-$ | 450,600 |
| 16 | $CH_3(CH_2)_6CO-$ | H | $CH_3(CH_2)_6CO-$ | >600 |
| 17 | $CH_3(CH_2)_9CO-$ | H | $CH_3(CH_2)_9CO-$ | 94 |
| 22 | $CH_3(CH_2)_{11}-$ | H | H | >300 |

[a]Administered intravenously,
[b]Two experiments

We claim:
1. An A-21978C cyclic peptide derivative of the formula:

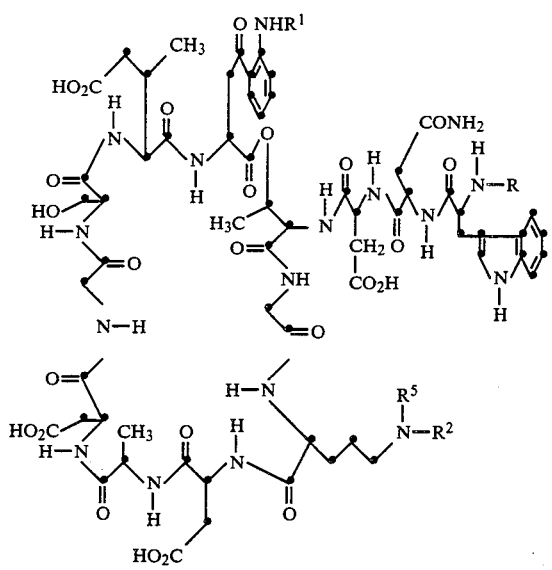

in which R, $R^1$ and $R^2$ are, independently, hydrogen, $C_4$–$C_{14}$-alkyl, optionally substituted $C_2$–$C_{19}$-alkanoyl, $C_5$–$C_{19}$-alkenoyl or an amino-protecting group; $R^3$, $R^4$ and $R^5$ are hydrogen or (i) $R^3$ and $R^1$ nd/or (ii) $R^4$ and R and/or (iii) $R^5$ and $R^2$, taken together, may represent a $C_4$–$C_{14}$ alkylidene group; provided that (1) at least one of R, $R^1$ or $R^2$ must be other than hydrogen or an amino-protecting group, (2) at least one of $R^1$ or $R^2$ must be hydrogen or an amino-protecting group, (3) the R, $R^1$ and $R^2$ groups must together contain at least four carbon atoms, and (4) when $R^1$ and $R^2$ are both selected from hydrogen or an amino-protecting group, R cannot be 8-methyldecanoyl, 10-methyldodecanoyl, 10-methylundecanoyl, the mixes $C_{10}$-alkanoyl group of A-21978$C_0$ or the specific $C_{12}$-alkanoyl groups of A-21978C factors $C_4$ and $C_5$; and the salts thereof.

2. A compound of claim 1 wherein R is $C_5$–$C_{19}$-alkanoyl and salts thereof.

3. A compound of claim 2 wherein R is alkanoyl of the formula

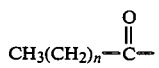

and n is an integer from 3 to 17; and the salts thereof.

4. A compound of claim 3 wherein $R^1$ and $R^2$ are hydrogen and the salts thereof.

5. The compound of claim 4 wherein R is heptanoyl and its salts.

6. The compound of claim 4 wherein R is octanoyl and its salts.

7. The compound of claim 4 wherein R is nonanoyl and its salts.

8. The compound of claim 4 wherein R is decanoyl and its salts.

9. The compound of claim 4 wherein R is undecanoyl and its salts.

10. The compound of claim 4 wherein R is lauroyl and its salts.

11. The compound of claim 4 wherein R is tridecanoyl and its salts.

12. The compound of claim 4 wherein R is myristoyl and its salts.

13. The compound of claim 4 wherein R is pentadecanoyl and its salts.

14. A compound of claim 2 wherein R is alkanoyl of the formula

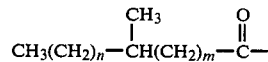

and n and m are each, independently, an integer from 0 to 14, provided that n+m must be no less than 1 and no greater than 15; and further provided that, when n is 0, m cannot be 8 and, when n is 1, m cannot be 6 or 8; and the salts thereof.

15. A compound of claim 14 wherein $R^1$ and $R^2$ are hydrogen and the salts thereof.

16. The compound of claim 15 wherein R is 8-methylundecanoyl and its salts.

17. A compound of claim 1 wherein R is $C_5$–$C_{19}$-alkenoyl and salts thereof.

18. A compound of claim 17 wherein R is cis or trans alkenyl of the formula

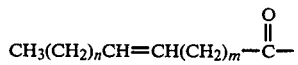

wherein n and m are each, independently, an integer of from 0 to 14, provided that n+m must be no less than 1 and no greater than 15; and the salts thereof.

19. A compound of claim 18 wherein $R^1$ and $R^2$ are hydrogen and salts thereof.

20. A compound of claim 17 wherein R is cis or trans alkenyl of the formula:

and salts thereof.

21. A compound of claim 20 wherein $R^1$ and $R^2$ are hydrogen and salts thereof.

22. A compound of claim 20 wherein R is 10-undecenoyl and its salts.

23. A compound of claim 1 wherein R and $R^4$ taken together represent $C_4$–$C_{14}$-alkylidenyl and salts thereof.

24. A compound of claim 23 wherein R is dodecylidenyl and salts thereof.

25. The compound of claim 24 wherein $R^1$ and $R^2$ are hydrogen and its salts.

26. A compound of claim 1 wherein R is $C_4$–$C_{14}$-alkyl and salts thereof.

27. A compound of claim 26 wherein R is dodecyl and salts thereof.

28. A compound of claim 27 wherein $R^1$ and $R^2$ are hydrogen and its salts.

29. The compound of claim 2 wherein R is $C_{10}$-alkanoyl.

30. The compound of claim 8 wherein R is n-decanoyl.

* * * * *

UNITED STATES PATENT AND TRADEMARK OFFICE
CERTIFICATE OF CORRECTION

PATENT NO. : 4,537,717
DATED : August 27, 1985
INVENTOR(S) : Bernard J. Abbott, Manuel Debono, David S. Fukuda It is certified that error appears in the above—identified patent and that said Letters Patent is hereby corrected as shown below:

Front page, under "ABSTRACT", that part of the structural formula appearing as

" 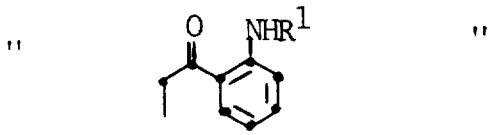 "

should read

-- 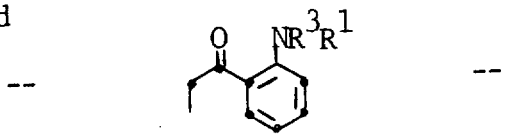 -- and that part of the structural formula appearing as

" 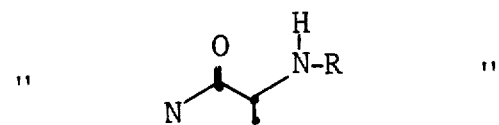 "

should read

-- 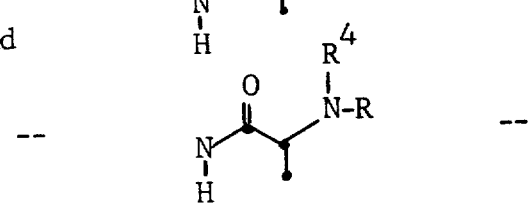 --

UNITED STATES PATENT AND TRADEMARK OFFICE
CERTIFICATE OF CORRECTION

PATENT NO. : 4,537,717

DATED : August 27, 1985

INVENTOR(S) : Bernard J. Abbott, Manuel Debono, David S. Fukuda

It is certified that error appears in the above—identified patent and that said Letters Patent is hereby corrected as shown below:

Column 1, line 18, that part of the structural formula appearing as

""

should read

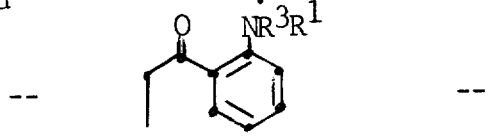

--  --

Column 1, line 23, that part of the structural formula appearing as

"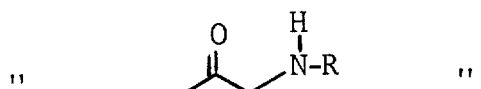"

should read

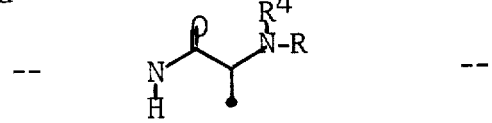

--  --

Column 4, line 43, "pepsininhibiting" should read -- pepsin-inhibiting --.

UNITED STATES PATENT AND TRADEMARK OFFICE
CERTIFICATE OF CORRECTION

PATENT NO. : 4,537,717   Page 3 of 6
DATED : August 27, 1985
INVENTOR(S) : Bernard J. Abbott, Manuel Debono, David S. Fukuda It is certified that error appears in the above—identified patent and that said Letters Patent is hereby corrected as shown below:

Column 7, line 30, that part of the structural formula appearing as

" " should read -- --

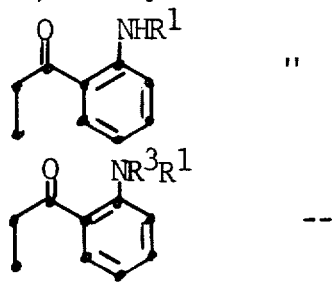

Column 7, line 35, that part of the structural formula appearing as

" " should read -- --

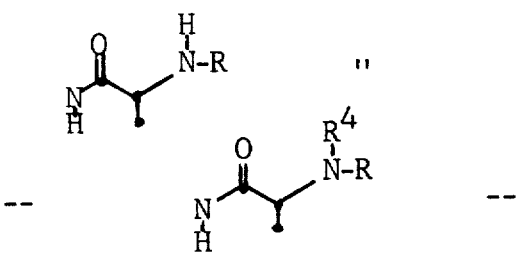

UNITED STATES PATENT AND TRADEMARK OFFICE
CERTIFICATE OF CORRECTION

PATENT NO. : 4,537,717
DATED : August 27, 1985
INVENTOR(S) : Bernard J. Abbott, Manuel Debono, David S. Fukuda It is certified that error appears in the above—identified patent and that said Letters Patent is hereby corrected as shown below:

Column 15, lines 19-21,

| Ingredient | Amount |
|---|---|
| MEDIUM A | | should read

| MEDIUM A | |
|---|---|
| Ingredient | Amount |

Column 15, line 33, "MEDIUM B" should read

| MEDIUM B | |
|---|---|
| Ingredient | Amount |

Column 19, line 25, "was carried out as de-" should not be in italics; line 26, "scribed in Preparation" should not be in italics.

Column 19, line 31, "$N_{Orn}\text{-}t\text{-}BOC\ complex$" should read -- $N_{Orn}\text{-}t\text{-}BOC$ complex --; "complex" should not be in italics.

Column 19, line 52, "$N_{Orn}\text{-}t\text{-}BOC\ nucleus$" should read -- $N_{Orn}\text{-}t\text{-}BOC$ nucleus --; "nucleus" should not be in italics.

UNITED STATES PATENT AND TRADEMARK OFFICE
CERTIFICATE OF CORRECTION

PATENT NO. : 4,537,717

DATED : August 27, 1985

INVENTOR(S) : Bernard J. Abbott, Manuel Debono, David S. Fukuda

It is certified that error appears in the above—identified patent and that said Letters Patent is hereby corrected as shown below:

Column 20, line 17, "6min." should read -- 6 min. --.

Column 22, line 18, that part of the structural formula appearing as

" " should read

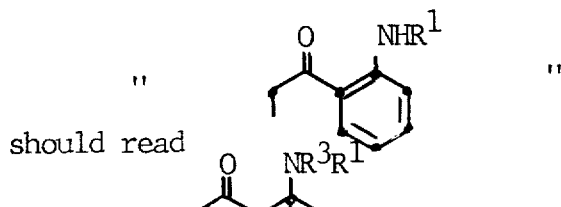

-- --

Column 22, line 22, that part of the structural formula appearing as

" " should read

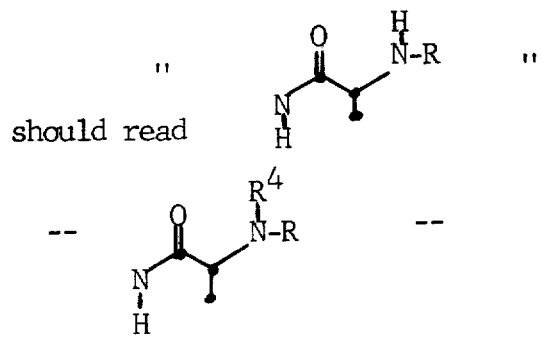

-- --

UNITED STATES PATENT AND TRADEMARK OFFICE
CERTIFICATE OF CORRECTION

PATENT NO. : 4,537,717

DATED : August 27, 1985

INVENTOR(S) : Bernard J. Abbott, Manuel Debono, David S. Fukuda

It is certified that error appears in the above—identified patent and that said Letters Patent is hereby corrected as shown below:

Column 33, line 6, that part of the structural formula appearing as

" 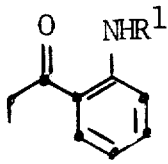 "   should read   -- 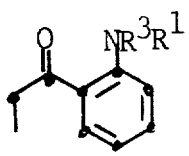 --

Column 33, line 10, that part of the structural formula appearing as

" 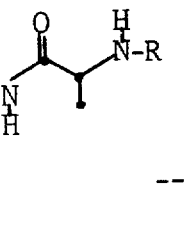 "   should read   -- 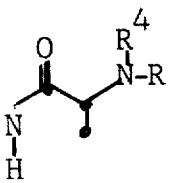 --

Column 33, line 31, "nd/or" should read -- and/or --; line 41, "mixes" should read -- mixed --.

Signed and Sealed this

Ninth Day of September 1986

[SEAL]

Attest:

DONALD J. QUIGG

Attesting Officer    Commissioner of Patents and Trademarks